US009526856B2

(12) United States Patent
Azagury et al.

(10) Patent No.: US 9,526,856 B2
(45) Date of Patent: Dec. 27, 2016

(54) DEVICES AND METHODS FOR PREVENTING TRACHEAL ASPIRATION

(71) Applicant: THE BOARD OF TRUSTEES OF THE LELAND STANFORD JUNIOR UNIVERSITY, Stanford, CA (US)

(72) Inventors: Dan E. Azagury, Geneva (CH); Mary K. Garrett, Redwood City, CA (US); David Gal, San Francisco, CA (US); Raymond Bonneau, San Francisco, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 528 days.

(21) Appl. No.: 13/714,124

(22) Filed: Dec. 13, 2012

(65) Prior Publication Data

US 2014/0000622 A1 Jan. 2, 2014

Related U.S. Application Data

(60) Provisional application No. 61/576,305, filed on Dec. 15, 2011, provisional application No. 61/599,614,
(Continued)

(51) Int. Cl.
*A61M 16/04* (2006.01)
*A61B 1/267* (2006.01)

(52) U.S. Cl.
CPC ....... *A61M 16/0434* (2013.01); *A61M 16/044* (2013.01); *A61M 16/0445* (2014.02);
(Continued)

(58) Field of Classification Search
CPC .............. A61M 16/04; A61M 16/0434; A61M 2016/0427; A61M 25/10; A61M 25/1011; A61M 2025/1015; A61M 2025/1084; A61M 2025/1088; A61B 17/12022; A61B 17/12136
(Continued)

(56) References Cited

U.S. PATENT DOCUMENTS 2,463,149 A 3/1949 Caine
2,541,402 A 2/1951 Caine
(Continued)

FOREIGN PATENT DOCUMENTS

EP 900048 3/1999
EP 1767182 3/2007
(Continued)

OTHER PUBLICATIONS

International Preliminary Report on Patentability received for PCT Patent Application No. PCT/US2014/064186 mailed on Nov. 24, 2015, 4 pages.
(Continued)

*Primary Examiner* — Lynne Anderson
*Assistant Examiner* — Kathryn E Ditmer
(74) *Attorney, Agent, or Firm* — Levine Bagade Han LLP

(57) ABSTRACT

Devices and methods for preventing tracheal aspiration as described where a cuff assembly having an inflatable member with an inflation tube fluidly coupled may be placed over a proximal end of an endotracheal tube or laryngeal mask and inserted into the patient trachea with the endotracheal tube or separately after the endotracheal tube has already been positioned. In either case, the inflatable member may be positioned distal (or inferior) to the vocal cords and proximal to the endotracheal balloon via a delivery instrument which automatically positions the balloon in proximity to the vocal cords.

38 Claims, 31 Drawing Sheets

Related U.S. Application Data filed on Feb. 16, 2012, provisional application No. 61/647,817, filed on May 16, 2012, provisional application No. 61/659,483, filed on Jun. 14, 2012.

(52) U.S. Cl.
CPC .... *A61M 16/0447* (2014.02); *A61M 16/0459* (2014.02); *A61M 16/0488* (2013.01); *A61B 1/267* (2013.01)

(58) Field of Classification Search
USPC ............. 128/200.24, 200.26, 207.14, 207.15
See application file for complete search history.

(56) References Cited

U.S. PATENT DOCUMENTS

| | | | |
|---|---|---|---|
| 3,516,408 A | 6/1970 | Vincent | |
| 3,538,918 A | 11/1970 | Engelesher et al. | |
| 3,760,811 A | 9/1973 | Andrew | |
| 3,792,701 A | 2/1974 | Kloz et al. | |
| 3,799,173 A | 3/1974 | Kamen | |
| 3,827,437 A | 8/1974 | Inaba | |
| 3,971,385 A | 7/1976 | Corbett | |
| 4,043,346 A | 8/1977 | Mobley et al. | |
| 4,091,816 A * | 5/1978 | Elam | 128/207.15 |
| 4,235,239 A | 11/1980 | Elam | |
| 4,244,362 A | 1/1981 | Anderson | |
| 4,256,099 A | 3/1981 | Dryden | |
| 4,273,128 A | 6/1981 | Lary | |
| 4,289,128 A | 9/1981 | Rusch | |
| 4,309,994 A | 1/1982 | Grunwald | |
| 4,341,210 A * | 7/1982 | Elam | 128/207.15 |
| 4,344,436 A | 8/1982 | Kubota | |
| 4,393,872 A | 7/1983 | Reznik et al. | |
| 4,416,273 A | 11/1983 | Grimes | |
| 4,416,289 A | 11/1983 | Bresler | |
| 4,431,005 A | 2/1984 | McCormick | |
| 4,445,501 A | 5/1984 | Bresler | |
| 4,447,227 A * | 5/1984 | Kotsanis | 604/95.03 |
| 4,449,522 A | 5/1984 | Baum | |
| 4,453,545 A | 6/1984 | Inoue | |
| 4,502,482 A | 3/1985 | DeLuccia et al. | |
| 4,567,882 A | 2/1986 | Heller | |
| 4,633,864 A | 1/1987 | Walsh | |
| 4,637,389 A | 1/1987 | Heyden | |
| 4,646,733 A | 3/1987 | Stroh et al. | |
| 4,658,818 A | 4/1987 | Miller et al. | |
| 4,685,457 A | 8/1987 | Donenfeld | |
| 4,690,138 A | 9/1987 | Heyden | |
| 4,712,551 A | 12/1987 | Rayhanabad | |
| 4,787,399 A | 11/1988 | Bonello et al. | |
| 4,819,664 A | 4/1989 | Nazari | |
| 4,827,925 A | 5/1989 | Vilasi | |
| 4,840,172 A | 6/1989 | Augustine et al. | |
| 4,840,173 A | 6/1989 | Porter | |
| 4,848,331 A | 7/1989 | Northway | |
| 4,881,542 A | 11/1989 | Schmidt et al. | |
| 4,896,667 A | 1/1990 | Magnuson et al. | |
| 4,943,770 A | 7/1990 | Ashley et al. | |
| 4,949,716 A | 8/1990 | Chenoweth | |
| 4,960,122 A | 10/1990 | Mizus | |
| 4,967,744 A | 11/1990 | Chua | |
| 4,969,878 A | 11/1990 | Schmidt et al. | |
| 4,976,261 A | 12/1990 | Gluck et al. | |
| 4,995,878 A | 2/1991 | Rai | |
| 5,003,963 A | 4/1991 | Bullard et al. | |
| 5,009,227 A | 4/1991 | Nieuwstad | |
| 5,010,892 A | 4/1991 | Colvin et al. | |
| 5,031,613 A | 7/1991 | Smith et al. | |
| 5,038,766 A * | 8/1991 | Parker | 128/200.26 |
| 5,042,469 A | 8/1991 | Augustine | |
| 5,080,104 A | 1/1992 | Marks et al. | |
| 5,095,896 A | 3/1992 | Omoigui | |
| 5,099,845 A | 3/1992 | Besz et al. | |
| 5,135,490 A | 8/1992 | Strickland | |
| 5,158,569 A | 10/1992 | Strickland et al. | |
| 5,163,941 A | 11/1992 | Garth et al. | |
| 5,165,420 A | 11/1992 | Strickland | |
| 5,174,283 A | 12/1992 | Parker | |
| 5,193,544 A | 3/1993 | Jaffe | |
| 5,199,427 A | 4/1993 | Strickland | |
| 5,203,320 A * | 4/1993 | Augustine | 600/187 |
| 5,218,957 A | 6/1993 | Strickland | |
| 5,230,332 A | 7/1993 | Strickland | |
| 5,231,983 A | 8/1993 | Matson et al. | |
| 5,235,970 A | 8/1993 | Augustine | |
| 5,242,389 A | 9/1993 | Schrader et al. | |
| 5,246,012 A | 9/1993 | Strickland | |
| 5,259,371 A * | 11/1993 | Tonrey | 128/200.26 |
| 5,259,377 A | 11/1993 | Schroeder | |
| 5,263,478 A | 11/1993 | Davis | |
| 5,273,534 A | 12/1993 | Knoepfler | |
| 5,285,778 A | 2/1994 | Mackin | |
| 5,316,024 A | 5/1994 | Hirschi et al. | |
| 5,329,940 A | 7/1994 | Adair | |
| 5,331,967 A | 7/1994 | Akerson | |
| 5,339,805 A | 8/1994 | Parker | |
| 5,359,999 A | 11/1994 | Kinsman | |
| 5,383,467 A | 1/1995 | Auer et al. | |
| 5,386,828 A | 2/1995 | Owens et al. | |
| 5,400,771 A | 3/1995 | Pirak et al. | |
| 5,405,325 A | 4/1995 | Labs | |
| 5,425,370 A | 6/1995 | Vilkomerson | |
| 5,425,382 A | 6/1995 | Golden et al. | |
| 5,445,144 A | 8/1995 | Wodicka et al. | |
| 5,445,161 A | 8/1995 | Huang | |
| 5,551,946 A | 9/1996 | Bullard | |
| 5,560,351 A | 10/1996 | Gravenstein et al. | |
| 5,588,424 A | 12/1996 | Insler et al. | |
| 5,622,169 A | 4/1997 | Golden et al. | |
| 5,626,128 A | 5/1997 | Bradley et al. | |
| 5,642,730 A | 7/1997 | Baran | |
| 5,645,065 A | 7/1997 | Shapiro et al. | |
| 5,660,175 A | 8/1997 | Dayal | |
| 5,665,052 A | 9/1997 | Bullard | |
| 5,669,924 A | 9/1997 | Shaknovich | |
| 5,672,179 A | 9/1997 | Garth et al. | |
| 5,701,918 A | 12/1997 | Jiraki | |
| 5,720,735 A | 2/1998 | Dorros | |
| 5,743,254 A | 4/1998 | Parker | |
| 5,765,559 A | 6/1998 | Kim | |
| 5,775,322 A | 7/1998 | Silverstein et al. | |
| 5,785,051 A | 7/1998 | Lipscher et al. | |
| 5,791,338 A | 8/1998 | Merchant et al. | |
| 5,800,342 A | 9/1998 | Lee et al. | |
| 5,803,898 A | 9/1998 | Bashour | |
| 5,840,013 A | 11/1998 | Lee et al. | |
| 5,842,973 A | 12/1998 | Bullard | |
| 5,853,004 A | 12/1998 | Goodman | |
| 5,865,176 A * | 2/1999 | O'Neil | 128/207.15 |
| 5,879,297 A | 3/1999 | Haynor et al. | |
| 5,902,238 A | 5/1999 | Golden et al. | |
| 5,913,816 A | 6/1999 | Sanders et al. | |
| 5,915,383 A | 6/1999 | Pagan | |
| 5,921,926 A | 7/1999 | Rolland et al. | |
| 5,954,636 A | 9/1999 | Schwartz et al. | |
| 5,975,697 A | 11/1999 | Podoleanu et al. | |
| 5,996,582 A | 12/1999 | Turnbull | |
| 6,063,022 A | 5/2000 | Ben-Haim | |
| 6,079,413 A | 6/2000 | Baran | |
| 6,129,668 A | 10/2000 | Haynor et al. | |
| 6,132,379 A | 10/2000 | Patacsil et al. | |
| 6,142,144 A | 11/2000 | Pacey | |
| 6,161,537 A | 12/2000 | Gravenstein et al. | |
| 6,164,277 A | 12/2000 | Merideth | |
| 6,202,646 B1 | 3/2001 | Camodeca et al. | |
| 6,216,028 B1 | 4/2001 | Haynor et al. | |
| 6,253,770 B1 | 7/2001 | Acker et al. | |
| 6,254,591 B1 | 7/2001 | Roberson | |
| 6,263,230 B1 | 7/2001 | Haynor et al. | |
| 6,332,089 B1 | 12/2001 | Acker et al. | |
| 6,349,720 B1 | 2/2002 | Clark | |
| 6,378,521 B1 | 4/2002 | Van Den Berg | |
| 6,415,787 B1 | 7/2002 | Boussignac | |

(56) References Cited

U.S. PATENT DOCUMENTS

| | | |
|---|---|---|
| 6,443,156 B1 | 9/2002 | Niklason et al. |
| 6,453,190 B1 | 9/2002 | Acker et al. |
| 6,460,540 B1 | 10/2002 | Klepper |
| 6,463,927 B1 | 10/2002 | Pagan |
| 6,485,500 B1 | 11/2002 | Kokish et al. |
| 6,513,527 B1 | 2/2003 | Abdel |
| 6,517,492 B2 | 2/2003 | Koblanski |
| 6,536,437 B1 | 3/2003 | Dragisic |
| 6,609,521 B1 | 8/2003 | Belani et al. |
| 6,634,360 B1 | 10/2003 | Flodin |
| 6,637,435 B2 | 10/2003 | Ciaglia et al. |
| 6,660,001 B2 | 12/2003 | Gregory |
| 6,668,198 B2 | 12/2003 | Swanson et al. |
| 6,668,832 B2 | 12/2003 | Hipolito et al. |
| 6,672,305 B2 | 1/2004 | Parker |
| 6,672,308 B1 | 1/2004 | Gaspari |
| 6,698,424 B2 | 3/2004 | Madsen et al. |
| 6,705,319 B1 | 3/2004 | Wodicka et al. |
| 6,729,334 B1 | 5/2004 | Baran |
| 6,761,693 B1 | 7/2004 | Rasmussen |
| 6,789,538 B2 | 9/2004 | Wright et al. |
| 6,799,574 B1 * | 10/2004 | Collins .................... 128/207.15 |
| 6,820,614 B2 | 11/2004 | Bonutti |
| 6,860,264 B2 | 3/2005 | Christopher |
| 6,889,693 B2 | 5/2005 | Hipolito et al. |
| 6,978,784 B2 | 12/2005 | Pekar |
| 7,013,890 B2 | 3/2006 | Wakabayashi |
| 7,089,928 B2 | 8/2006 | Besharim et al. |
| 7,124,755 B2 | 10/2006 | Van Hooser |
| 7,147,252 B2 | 12/2006 | Teuscher et al. |
| 7,179,220 B2 | 2/2007 | Kukuk |
| RE39,508 E | 3/2007 | Parker |
| 7,258,120 B2 | 8/2007 | Melker |
| 7,320,319 B2 | 1/2008 | Bonutti |
| 7,469,700 B2 | 12/2008 | Baran |
| 7,472,705 B2 | 1/2009 | Baran |
| 7,516,741 B2 | 4/2009 | Glusker et al. |
| 7,552,729 B2 | 6/2009 | O'Mara |
| 7,585,836 B2 | 9/2009 | Goodson et al. |
| 7,591,830 B2 | 9/2009 | Rutter |
| 7,691,397 B2 | 4/2010 | Brown et al. |
| 7,766,961 B2 | 8/2010 | Patel et al. |
| 7,771,401 B2 | 8/2010 | Hekmat et al. |
| 7,900,634 B2 | 3/2011 | Tjong |
| 7,913,693 B2 | 3/2011 | Nelson et al. |
| 7,914,503 B2 | 3/2011 | Goodson et al. |
| 7,914,517 B2 | 3/2011 | Baran et al. |
| 7,921,847 B2 | 4/2011 | Totz |
| 7,925,339 B2 | 4/2011 | Wik |
| 7,950,393 B2 | 5/2011 | Colburn et al. |
| 7,975,700 B2 | 7/2011 | Frazier et al. |
| 7,992,562 B2 | 8/2011 | Chen |
| 7,992,567 B2 | 8/2011 | Hirotsuka et al. |
| 7,993,325 B2 | 8/2011 | Elkins et al. |
| 7,997,266 B2 | 8/2011 | Frazier et al. |
| 8,006,697 B2 | 8/2011 | Boussignac |
| 8,010,180 B2 | 8/2011 | Quaid et al. |
| 8,012,121 B2 | 9/2011 | Goodson et al. |
| 8,042,544 B2 | 10/2011 | Ward et al. |
| 8,096,303 B2 | 1/2012 | Dineen et al. |
| 8,116,858 B2 | 2/2012 | Koblanski |
| 8,189,886 B2 | 5/2012 | Huo et al. |
| 8,196,584 B2 | 6/2012 | Maguire et al. |
| 8,231,524 B2 | 7/2012 | Schwartz et al. |
| 8,231,606 B2 | 7/2012 | Stenzler et al. |
| 8,244,329 B2 | 8/2012 | Su |
| 8,280,489 B2 | 10/2012 | Li et al. |
| 8,307,830 B2 | 11/2012 | Clayton |
| 8,336,541 B2 | 12/2012 | Schwartz et al. |
| 8,371,307 B2 | 2/2013 | Hirotsuka et al. |
| 8,425,455 B2 | 4/2013 | Nentwick |
| 8,434,487 B2 | 5/2013 | Nelson et al. |
| 8,457,715 B2 | 6/2013 | McKenna et al. |
| 8,457,716 B2 | 6/2013 | Li et al. |
| 8,468,637 B2 | 6/2013 | Vazales et al. |
| 8,479,739 B2 | 7/2013 | Hirsh |
| 8,505,531 B2 | 8/2013 | Pecherer et al. |
| 8,518,011 B2 | 8/2013 | Goodson et al. |
| 8,522,787 B2 | 9/2013 | Lin et al. |
| 8,577,108 B2 | 11/2013 | Huo et al. |
| 2002/0029031 A1 | 3/2002 | Bagaoisan et al. |
| 2002/0074002 A1 | 6/2002 | Tung et al. |
| 2002/0117171 A1 * | 8/2002 | Parker ..................... 128/200.26 |
| 2002/0143380 A1 | 10/2002 | Dahl et al. |
| 2003/0066532 A1 | 4/2003 | Gobel |
| 2003/0121521 A1 | 7/2003 | Hipolito et al. |
| 2004/0000314 A1 | 1/2004 | Angel |
| 2004/0039252 A1 | 2/2004 | Koch |
| 2004/0221853 A1 | 11/2004 | Miller |
| 2005/0038419 A9 | 2/2005 | Arnold et al. |
| 2005/0113701 A1 | 5/2005 | Chin et al. |
| 2005/0177024 A1 | 8/2005 | Mackin |
| 2006/0036164 A1 | 2/2006 | Wilson et al. |
| 2006/0081255 A1 | 4/2006 | Miller et al. |
| 2006/0107962 A1 | 5/2006 | Ward et al. |
| 2006/0207602 A1 | 9/2006 | Kolobow et al. |
| 2007/0017527 A1 | 1/2007 | Totz |
| 2007/0137652 A1 | 6/2007 | Qureshi et al. |
| 2007/0169780 A1 | 7/2007 | Halpern et al. |
| 2007/0185444 A1 * | 8/2007 | Euteneuer et al. ........ 604/96.01 |
| 2008/0039715 A1 | 2/2008 | Wilson et al. |
| 2008/0078403 A1 | 4/2008 | Clayton |
| 2008/0140106 A1 | 6/2008 | McGrath |
| 2008/0156323 A1 | 7/2008 | Angel et al. |
| 2008/0216827 A1 * | 9/2008 | Seydel et al. ............ 128/200.26 |
| 2008/0236593 A1 | 10/2008 | Nelson et al. |
| 2008/0262428 A1 | 10/2008 | Gobel |
| 2008/0273209 A1 | 11/2008 | Delfyett |
| 2009/0032027 A1 | 2/2009 | McCachren et al. |
| 2009/0125002 A1 | 5/2009 | Totz |
| 2009/0143645 A1 | 6/2009 | Matthes |
| 2009/0171293 A1 | 7/2009 | Yang et al. |
| 2009/0229615 A1 | 9/2009 | Stenzler et al. |
| 2010/0006102 A1 | 1/2010 | Schnell et al. |
| 2010/0059048 A1 | 3/2010 | O'Mara |
| 2010/0113916 A1 | 5/2010 | Kumar |
| 2010/0145192 A1 | 6/2010 | Elgort et al. |
| 2010/0179417 A1 | 7/2010 | Russo |
| 2010/0180737 A1 * | 7/2010 | Klepper ............................ 83/39 |
| 2010/0186211 A1 | 7/2010 | Macan et al. |
| 2010/0186749 A1 | 7/2010 | Macan et al. |
| 2010/0208270 A1 | 8/2010 | Kulkarni et al. |
| 2010/0212671 A1 | 8/2010 | Miller et al. |
| 2010/0249639 A1 * | 9/2010 | Bhatt ........................... 600/546 |
| 2011/0023887 A1 | 2/2011 | Vazales et al. |
| 2011/0031961 A1 | 2/2011 | Durand et al. |
| 2011/0048427 A1 * | 3/2011 | Zachar .................... 128/207.15 |
| 2011/0098720 A1 | 4/2011 | Taylor et al. |
| 2011/0146690 A1 * | 6/2011 | Wood et al. ............. 128/207.14 |
| 2011/0213214 A1 | 9/2011 | Finneran et al. |
| 2011/0265797 A1 | 11/2011 | Waldron |
| 2012/0006331 A1 | 1/2012 | Ward et al. |
| 2012/0125346 A1 | 5/2012 | Clayton et al. |
| 2013/0103163 A1 | 4/2013 | Krimsky et al. |
| 2013/0253310 A1 | 9/2013 | McKenna et al. |

FOREIGN PATENT DOCUMENTS

| | | |
|---|---|---|
| EP | 2517622 | 10/2012 |
| EP | 2524713 | 11/2012 |
| GB | 2098485 | 11/1982 |
| SU | 124593 | 11/1959 |
| SU | 908371 | 2/1982 |
| WO | WO 8602564 | 5/1986 |
| WO | WO 8602848 | 5/1986 |
| WO | WO 8806903 | 9/1988 |
| WO | WO 9210971 | 7/1992 |
| WO | WO 9316752 | 9/1993 |
| WO | WO 9823317 | 6/1998 |
| WO | WO 9836684 | 8/1998 |
| WO | WO 9841272 | 9/1998 |
| WO | WO 0191843 | 12/2001 |
| WO | WO 0247748 | 6/2002 |
| WO | WO 02065903 | 8/2002 |

(56) References Cited

FOREIGN PATENT DOCUMENTS

| WO | WO 02070038 | 9/2002 |
|---|---|---|
| WO | WO 03015610 | 2/2003 |
| WO | WO 2006018163 | 2/2006 |
| WO | WO 2007035297 | 3/2007 |
| WO | WO 2007088539 | 8/2007 |
| WO | WO 2008136658 | 11/2008 |
| WO | WO 2009026095 | 2/2009 |
| WO | WO 2009045378 | 4/2009 |
| WO | WO 2009099766 | 8/2009 |
| WO | WO 2010062603 | 6/2010 |
| WO | WO 2010091462 | 8/2010 |
| WO | WO 2010117999 | 10/2010 |
| WO | WO 2010118005 | 10/2010 |
| WO | WO 2011022802 | 3/2011 |
| WO | WO 2012138388 | 10/2012 |
| WO | WO 2013/090619 | 6/2013 |
| WO | WO 2013118059 | 8/2013 |

OTHER PUBLICATIONS

International Search Report and Written Opinion received for PCT Patent Appiication No. PCT/US2014/064179 mailed on Feb. 18, 2015, 9 pages.
International Search Report and Written Opinion received for PCT Patent Application No. PCT/US2014/064186 mailed on Feb. 10, 2015, 9 pages.

* cited by examiner

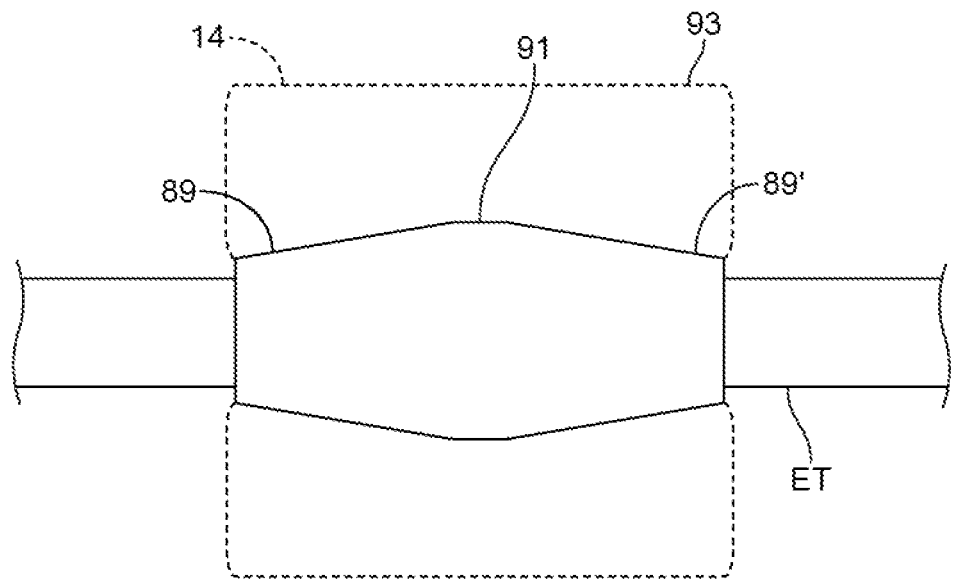
FIG. 5E
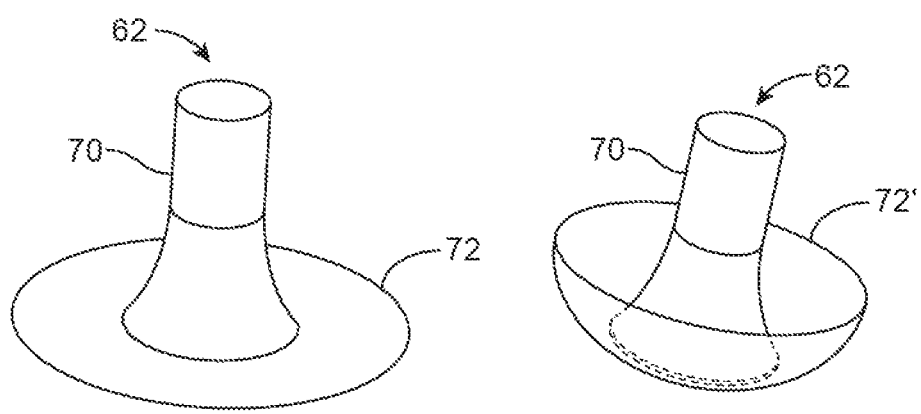
FIG. 6A
FIG. 6B

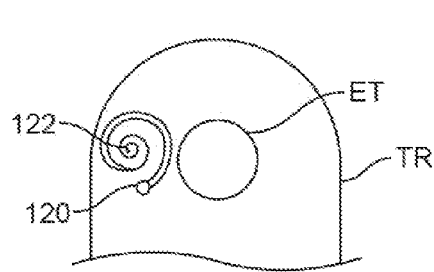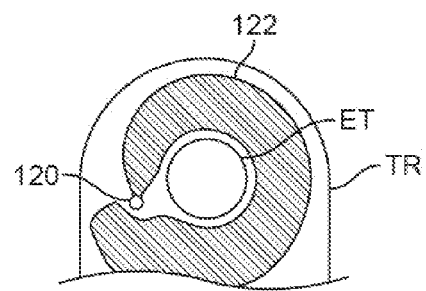
FIG. 12A     FIG. 12B
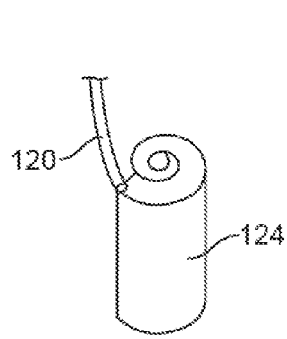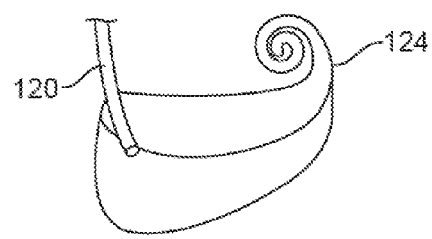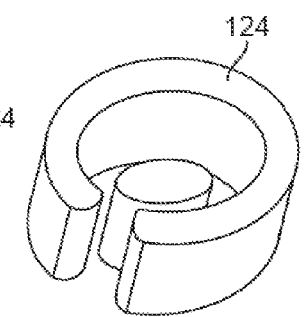
FIG. 13A     FIG. 13B     FIG. 13C
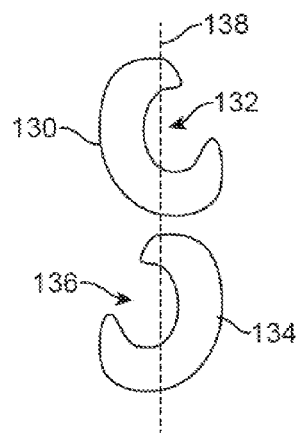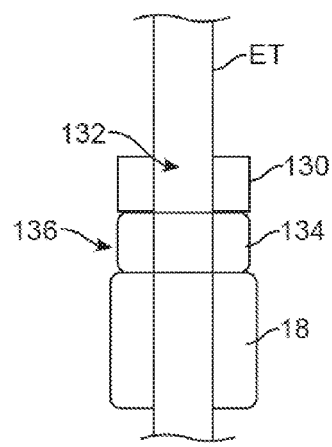
FIG. 14A     FIG. 14B

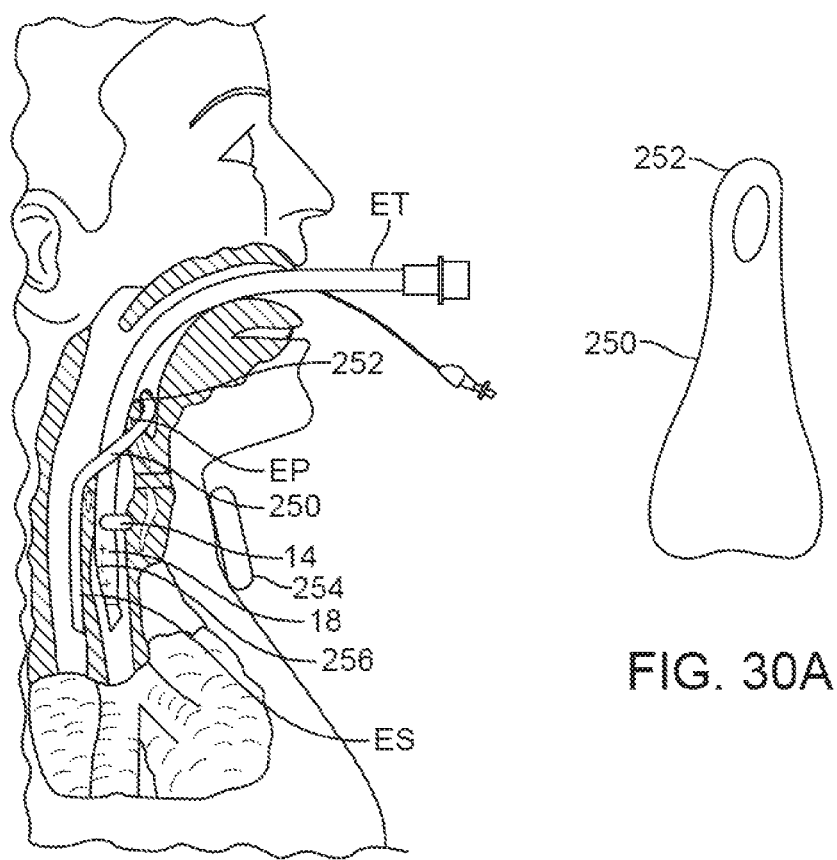
FIG. 29
FIG. 30A
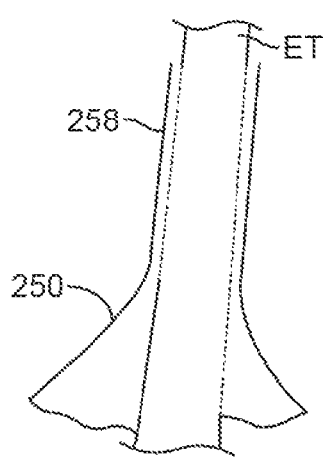
FIG. 30B
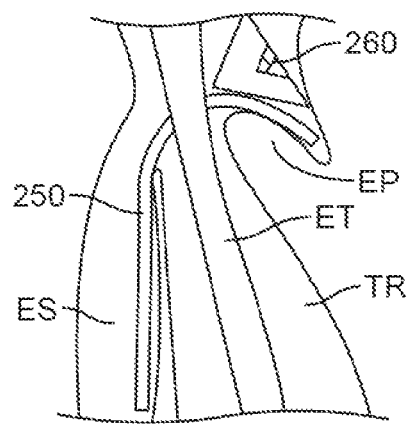
FIG. 30C

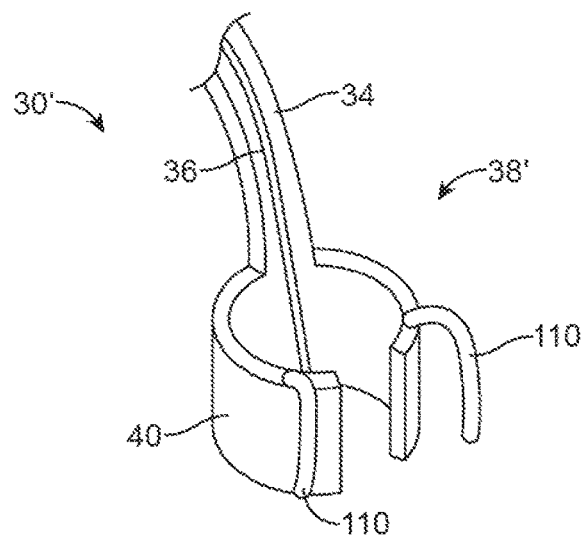
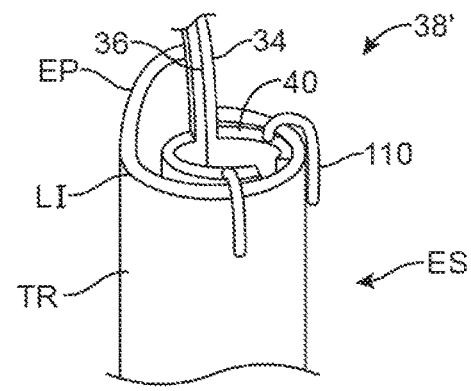
FIG. 31A    FIG. 31B
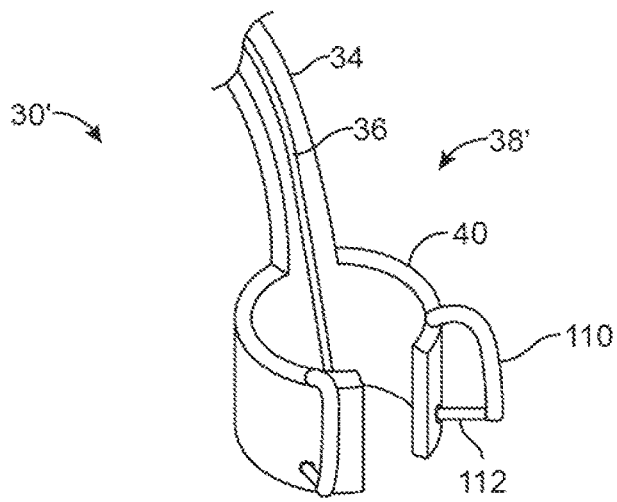
FIG. 31C

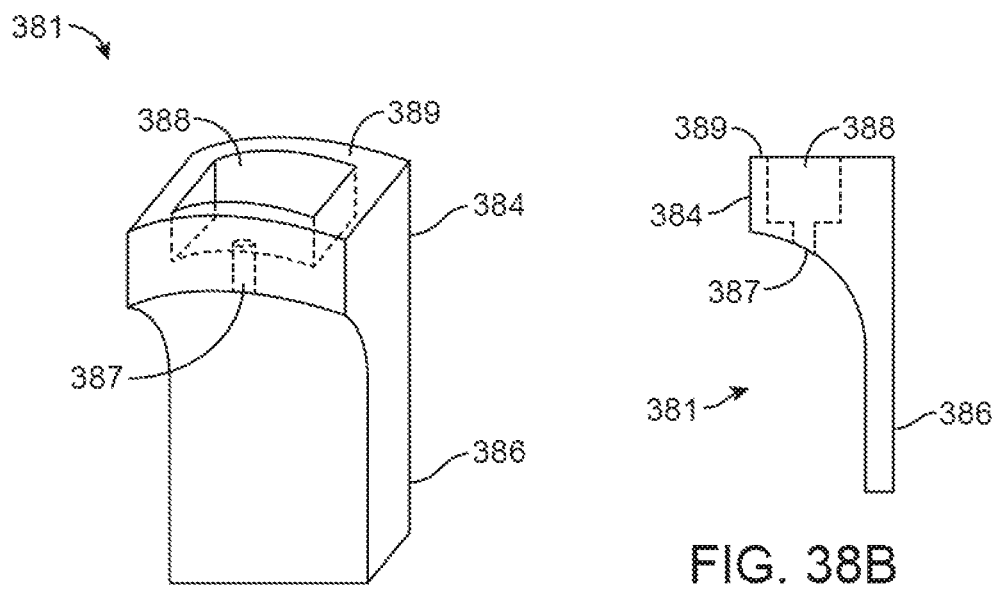
FIG. 38A
FIG. 38B
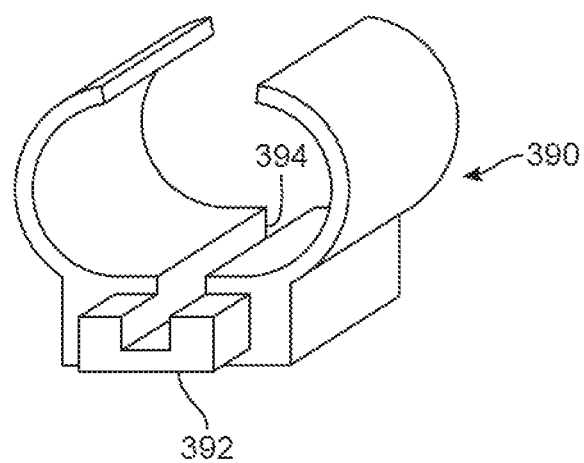
FIG. 39

DEVICES AND METHODS FOR PREVENTING TRACHEAL ASPIRATION

CROSS-REFERENCE TO RELATED APPLICATIONS

This application claims the benefit of priority to U.S. Provisional Applications 61/576,305 filed Dec. 15, 2011; 61/599,614 filed. Feb. 16, 2012; 61/647,817 filed May 16, 2012; and 61/659,483 filed Jun. 14, 2012, each of which is incorporated herein by reference in its entirety.

FIELD OF THE INVENTION

The present invention relates to devices and methods for preventing tracheal aspiration. More particularly, the present invention relates to devices and methods for preventing tracheal aspiration in patients who are intubated to prevent conditions such as ventilator associated pneumonia (VAP).

BACKGROUND OF THE INVENTION

Patients who are intubated with an endotracheal (ET) tube are typically intubated to facilitate mechanical ventilation but are also associated with an increase in morbidity. Because ET tubes generally utilize an inflatable balloon between the tube and the walls of the trachea to prevent aspiration or passage of fluids and debris into the trachea, small pools of pathogen-containing secretions may pool in the sub-glottic space. Small channels sometimes develop between the balloon walls and the walls of the trachea through which debris and subglottic secretions pass into the lower respiratory tract.

Prior devices have attempted to clear or prevent the aspiration of the debris and secretions such as endotracheal tubes which drain the fluid via suction; however, such devices may require intermittent suctioning and further require specialized ET tubes. Other previous devices have utilized balloon cuff designs which have varying configurations yet such devices require the purchase and use of these specific ET tubes. These devices utilizing ET tubes require their use at the time of intubation and indiscriminately across all patients which make them prohibitively expensive for many medical facilities.

Additional prior devices have utilized the infusion or introduction of obstructing materials such as gels, foams, polymers, etc. in the sub-glottic space in proximity to the inflatable ET balloon or in place of the balloon itself. However, such materials may present difficulty in removal from the patient's airway and may also present the possibility of inadvertent aspiration itself.

Accordingly, there exists a need for devices and methods which allow for rapid deployment into a patient and which may also be used in con unction with conventional ET tubes which are already in wide use.

SUMMARY OF THE INVENTION

With an ET tube positioned within a patient's trachea or a laryngeal mask positioned within the patient's airway, a deployable member may be deployed to form a barrier within or along the patient's airway, which may prevent liquid, solid, or particulate matter from passing into the trachea. The deployable member may be inflatable or expandable, and may be inserted over or around the ET tube and/or laryngeal mask. In some instances, the deployable member may comprise a cuff assembly, and may either be deployed simultaneously with the ET tube during intubation or post-intubation once the ET tube has already been placed within the patient. The cuff assembly may be delivered using a delivery instrument. Generally, such a delivery instrument may comprise an elongate shaft that is formed with a curvature or is capable of defining a curvature which presents an atraumatic profile for per-oral insertion into a trachea of a subject, a distal stop or other stopping mechanism (e.g., one or more hook members) attached to a distal end of the shaft where the distal stop is sized to prevent passage of the distal stop through the vocal cords, the laryngeal inlet (e.g., upon the corniculate cartilage and cuneiform cartilage of the larynx), or another suitable tissue of the subject, and a cuff engagement member which extends distally from the distal stop and/or the shaft and forms an edge for engagement with a cuff assembly. The distal stop and/or cuff engagement member may define an opening sized to receive an endotracheal tube therealong. In some instances, the distal stop may be transversely oriented relative to the shaft.

A cuff assembly may comprise an inflatable or expandable member and an inflation tube fluidly coupled thereto, and may be placed over a proximal end of the ET tube (and/or a laryngeal mask) and either inserted into the patient trachea with the ET tube or separately after the ET tube has already been positioned. In either case, the inflatable member may be positioned distal (or inferior) to the vocal cords and proximal to the ET balloon via a delivery instrument where the inflatable member may be inflated or expanded into contact against the walls of the trachea via an inflation port located external to the patient and fluidly coupled via the inflation tube to the inflatable member.

Once the inflatable member has been inflated, it may provide an additional seal or barrier to any debris or fluids from being aspirated or drawn into the trachea. The inflatable member may be positioned anywhere along the ET tube (e.g., within the trachea inferior or superior to the vocal cords or even superior to the epiglottis, such as against the pharyngeal tissue walls if so desired). Alternatively, the inflatable member may be placed within the vocal cords and expanded to gently conform against the vocal cord tissues.

In order to urge or translate an inflatable member along or over an ET tube, a delivery instrument may engage or otherwise attach to the inflatable member, and may be manipulated to selectively advance and position the inflatable member. The delivery instrument may comprise a handle from which an arcuate or curved shaft may extend and a distal engagement portion positioned at a distal end of shaft. Because the arcuate or curved shaft may be advanced through the mouth and/or trachea of a patient, the shaft may define a gentle curvature and present an atraumatic profile to the anatomy of the trachea. In alternative variations, the shaft may be formed without a curve, but may be flexible member and conform to the patient's anatomy. The shaft may also define a receiving channel for positioning and securement of the inflation tube along the length of shaft during advancement and delivery of inflation member.

While the inflatable member may slide over or along the ET tube prior to inflation of the inflatable member, the delivery instrument may be removed from the ET tube once the inflatable member has been desirably positioned. Thus, the distal engagement portion may be configured to have a cuff engagement member which forms a structure which extends distally from the shaft and forms a partially tubular member which may extend peripherally away from the curvature of shaft. The cuff engagement member may also form an edge or lip at its distal end for engagement with the inflatable member, and may slidingly receive the ET tube.

Moreover, because of its open structure, the shaft may be placed against and/or removed from the ET tube anywhere along its length without having to be removed from the proximal end of the ET tube. Additionally, a distal stop forming a ledge or surface may extend circumferentially along a proximal portion of the cuff engagement member and may also project away from the curvature of shaft.

With the distal stop extending radially outward relative to the shaft, the distal stop may guide the placement of the inflatable member relative to the patient's vocal cords and the ET balloon. Because the cuff engagement member may extend distally from the distal stop at a specified distance, as the handle is advanced along the ET tube within the patient, the inflatable member may be pushed or urged distally until the distal stop bumps against the vocal cords, laryngeal inlet, or another target tissue of a patent which may prevent further advancement of the delivery instrument and inflatable member and may position the inflatable member that specified distance beyond the vocal cords, laryngeal inlet, or other target tissue. The distal stop and cuff engagement member may be rounded and present atraumatic surfaces to the tissue. The stop may provide tactile feedback to the practitioner indicating that the inflatable member has been positioned beyond and cleared the vocal cords by the distance of the cuff engagement member distal to the distal stop without requiring any direct visualization or imaging of the tissue or inflatable member. Hence, the inflatable member may be positioned simply by advancing the inflatable member along the ET tube until the distal stop abuts the vocal cords, which may automatically position the inflatable member below or inferior to the vocal cords. In other instances, in addition to or as an alternative of tactile feedback, other forms of feedback may be utilized such as an imaging device positioned along the shaft, inflatable member, ET tube, etc. (e.g., optical fibers, CCD imagers, CMOS imagers, etc.) or via a separate imaging instrument (e.g., a laryngoscope or endoscope). Additionally, other forms of feedback such as a fluid column which is raised as the stop abuts the vocal cords, pressure sensors, electrical impedance sensors, etc. may be used to provide an alert or indication to the user that distal engagement portion of the delivery device has reached or is near the vocal cords, laryngeal inlet, or another specified tissue area.

In alternative variations, the distal stop may be formed into various configurations and shapes which provide for a stopping mechanism against the vocal cords and/or the laryngeal inlet. Any of these variations may be used in combination with the devices and methods described herein.

The distal edge or lip of the cuff engagement member may define a cuff engagement lip which may have a relatively smaller diameter than the cuff engagement member such that the cuff engagement lip may nestle or abut an inner edge of the inflatable member (e.g., an inner edge of an inflation ring of the inflatable member). Tension by the inflation tube along the shaft may provide for a gentle force proximally to secure the inflation ring to the engagement lip during advancement and positioning along the ET tube. To release the inflatable member from the delivery instrument, the lumen may be disengaged and the handle may be pulled proximally either prior to, during, or after inflation of the inflatable member to release the inflatable member and leaving it positioned along the ET tube.

In yet other variations of the cuff assembly, the inflatable member may be shaped into any number of other suitable configurations. For example, the inflatable member may comprise an inversely tapered balloon or tapered to narrow away from the vocal cords. Another variation may include a balloon which may be wrapped about itself in a low-profile for delivery but when inflated via inflation tube may unwind within the trachea. Aside from utilizing a single inflatable member, multiple inflatable members may be used as an alternative. Yet another variation may include a helically-shaped balloon or a rotatable inflation tube. Another variation may include one or more discs each having a respective opening (e.g., a trapezoidal opening) that when stacked, along a longitudinal centerline as a disc assembly in staggered manner may create a seal.

In this variation and in each of the variations described, the cuff assembly may be utilized in any number of combinations as practicable. For example, the cuff assembly and delivery instrument may be utilized with any of the variations described in any number of combinations.

Aside from the use of inflatable members or stacked discs, the cuff assembly may also be utilized in combination with one or more biocompatible, hydrophilic or hydrophobic materials such as gel, polymer, poloxamer, foam, solid, etc. along with an ET tube. Such a substance could change state between solid, gel, liquid or vapor depending upon various factors such as temperature, pH, humidity, or could be triggered by external mechanisms such as electrical current, chemical reaction with a substrate, interaction with another substance such as an endotracheal tube or balloon coating. The substance may also be impregnated with various active agents such as antibacterial, antibiotic, antiviral, antifungal, bacteriostatic, or disinfectant substances in order to diffuse local. Additionally and/or alternatively, a shield having a securement member may be deployed within the patient in combination with the inflatable member and ET tube as well.

BRIEF DESCRIPTION OF THE DRAWINGS

FIGS. 5A to 5C show perspective, top, and side views of one variation of an inflation ring that a balloon may be attached to.

FIG. 5E shows a side view of yet another variation of an inflation ring having tapered distal and proximal ends.

FIGS. 6A and 6B show perspective views of another variation of a reconfigurable obstructing member.

FIGS. 12A and 12B show top views of yet another variation of a balloon which may be expanded into a tubular configuration.

FIGS. 13A to 13C show perspective views of another variation of a balloon.

FIGS. 14A and 14B show perspective and side views of yet another variation of the balloon which may be comprised of two or more off-set inflatable members.

FIG. 29 shows a side view of yet another variation for a reconfigurable mask or barrier which may be secured to an anatomy of the patient for obstructing the tracheal opening.

FIGS. 30A to 30C show front and side views of additional variations for reconfigurable barriers.

FIGS. 31A to 31C show perspective views of variations of delivery instruments having book members.

FIGS. 38A and 38B show a perspective view and a side view of a variation of an inflation ring.

FIG. 39 shows a bottom perspective view of a variation of a cuff engagement member for use with the delivery instruments described here.

DETAILED DESCRIPTION OF THE INVENTION

In preventing conditions such as VAP from occurring in an intubated patient, various deployable mechanisms described herein may be used with any number of conventional ET tubes or with specially configured ET tubes as well. With the ET tube positioned within the patient's trachea, a barrier may be formed within or along the patient's airway which may prevent liquid, solid, or particulate matter from passing through the vocal cords and into the trachea to inhibit or prevent microaspiration, aspiration, and aspiration pneumonia. Hence, a deployable member may be positioned along an ET tube to reside, for instance, at the opening of the larynx, vestibule, vocal cords, or elsewhere along the airway. The deployable member, which in some variations may be inflatable or expandable, may be inserted either simultaneously with the ET tube during intubation or post-intubation once the ET tube has already been placed within the patient. Additionally or alternatively, a deployable member may be positioned along a laryngeal mask to reside along the airway, as described here, and may be placed simultaneously with the laryngeal mask or advanced along the laryngeal mask after placement thereof.

Figure 1:
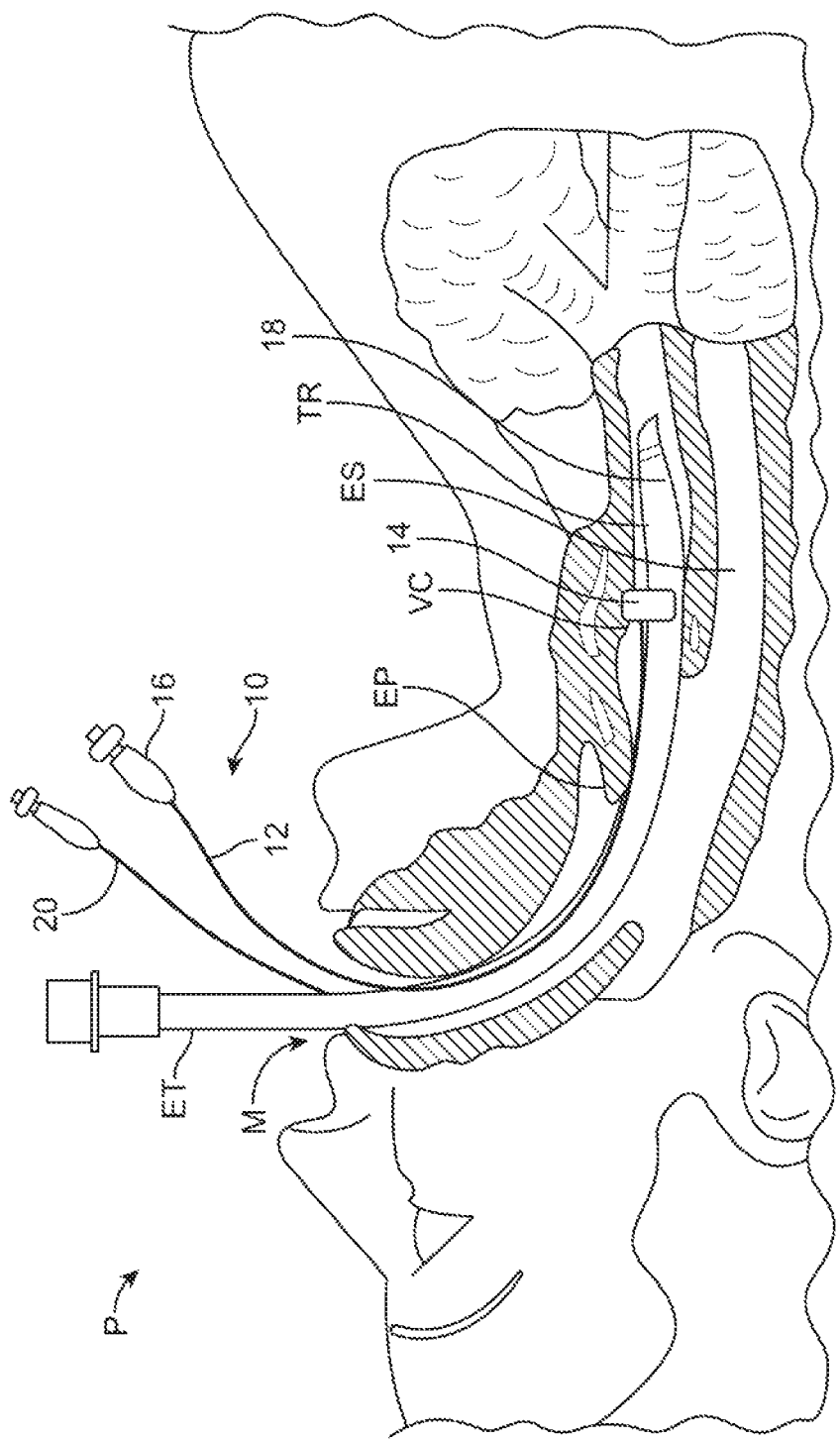
FIG. 1 shows an example of an inflatable cuff assembly which may be advanced over or along an ET tube into a position in the airway of a patient.

One example is shown in the side view of FIG. 1 which illustrates an ET tube ET which has been inserted through the mouth M of a patient P and advanced past the epiglottis EP and into the trachea TR. Also shown there is esophagus ES. The ET tube ET may comprise an ET balloon 18, which may be seen in FIG. 1 as being positioned past the vocal cords VC. The vocal cords are generally formed from ligaments overlaid by and connected to mucosal tissue and cartilage. Also shown there is an ET inflation tube 20 fluidly coupled to the ET balloon 18 for inflating the balloon 18 into contact against the walls of the trachea TR. A cuff assembly 10 having an inflatable or expandable member 14 with an inflation tube 12 fluidly coupled thereto may be placed over a portion of the ET tube ET. The inflatable member 14 may be positioned distal (or inferior) to the vocal cords VC and proximal to the ET balloon 18, as shown, via a delivery instrument (such as described below), and the inflatable member 14 may be inflated or expanded into contact against the walls of the trachea TR via an inflation port 16 located external to the patient and fluidly coupled via the inflation tube 12 to the inflatable member 14. Inflation of the inflatable member 14 may be done after, before, or simultaneously with inflation of the ET balloon 18. Additionally, the cuff assembly 10 may be placed over a proximal end of the ET tube ET and either inserted into the patient trachea TR during advancement of the ET tube ET or inserted separately after the ET tube ET has already been positioned.

Once the inflatable member 14 has been inflated, it may provide an additional seal or barrier to any debris or fluids from being aspirated or drawn into the trachea TR. Moreover, although the inflatable member 14 is illustrated in FIG. 1 as positioned past or inferior to the vocal cords VC, because the inflatable member 14 may be selectively moveable along the length of the ET tube ET, the inflatable member 14 may be placed anywhere along ET tube ET. For example, the inflatable member 14 may be positioned within the trachea TR inferior or superior to the vocal cords VC, or may be placed within the vocal cords VC and expanded to gently conform against the vocal cord tissue. Alternatively, the inflatable member 14 may be positioned superior to the epiglottis EP, such as against the pharyngeal tissue walls if so desired.

As mentioned above, a delivery instrument may be used to selectively advance and position the member 14. The delivery instrument may engage or otherwise attach to the inflatable member 14, and may be manipulated to urge or translate the inflatable member 14 along or over the ET tube ET. One variation of the delivery devices described here is shown in the perspective view of FIG. 2A. As shown there, the delivery instrument 30 may comprise a handle 32 from which a shaft 34 may extend, and a distal engagement portion 38 positioned at a distal end of the shaft 34. Also shown there is the ET tube ET and cuff assembly 10 described above with respect to FIG. 1, FIG. 2B also shows a perspective of the cuff assembly 10 and delivery instrument 30 removed from the ET tube ET for clarity. The inflatable member 14 may be seen in its expanded configuration while remaining attached to the delivery instrument 30.

The shaft 34 is preferably curved during advancement of the inflatable member 14. In some variations, the shaft 34 may have a permanent curvature (e.g., may be pre-formed with one or more curves). In other variations, the shaft 34 may be flexible, such that the shaft 34 may take on a specific curvature or otherwise conform to the patient's anatomy when a pushing force is applied to the handle 32. In some of these variations, the shaft 34 may be straight, but may flex or bend when a pushing force is applied to the handle 32.

Figure 2A:
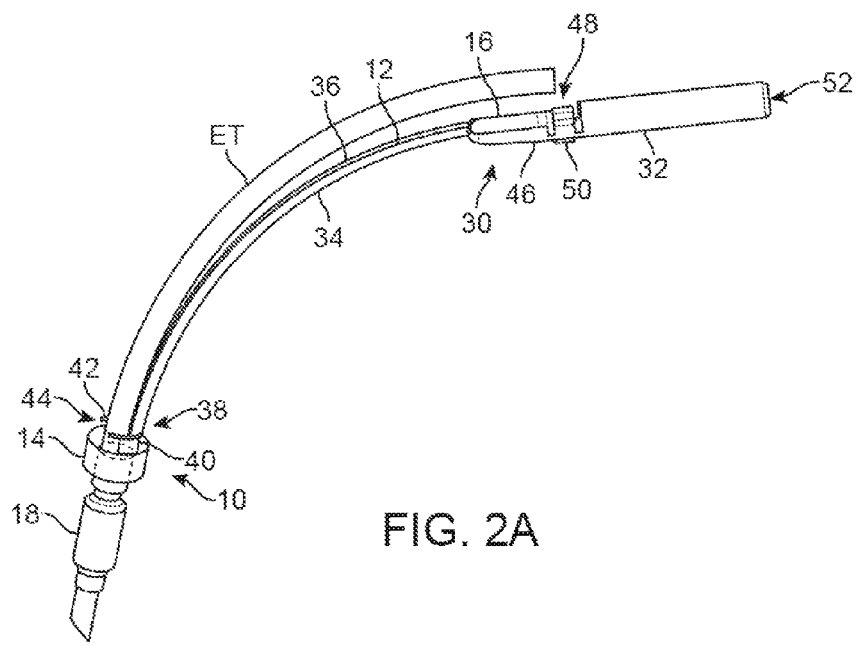
FIG. 2A shows a side view of an inflatable cuff assembly secured to a delivery instrument which may be slid along an ET tube for positioning an inflatable member in the airway of a patient.
Figure 2B:
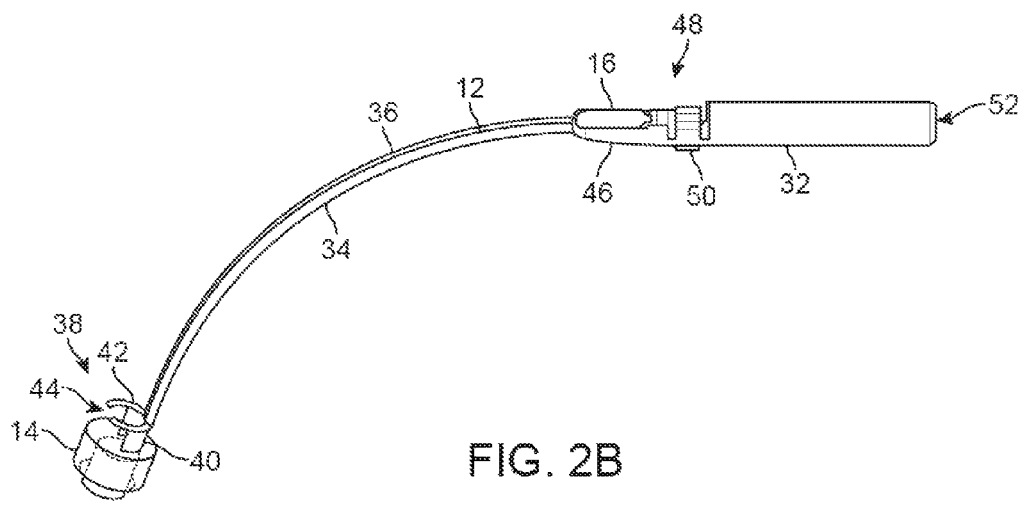
FIG. 2B shows a side view of the inflatable cuff assembly and delivery instrument removed from an ET tube for clarity.
Figure 2C:
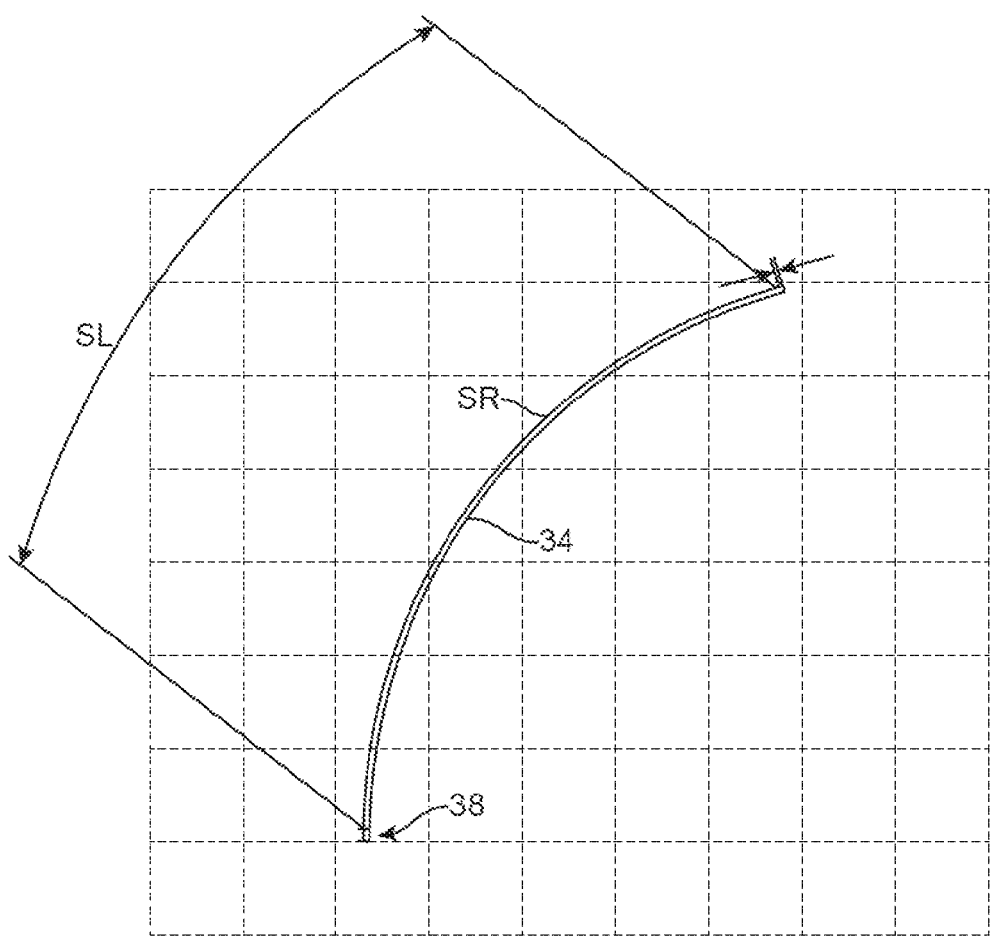
FIG. 2C shows a side view of the delivery instrument to illustrate its curvature and length.

When a curved shaft 34 is advanced through the mouth M and/or trachea TR of a patient P to urge the inflatable member 14 along the ET tube ET, the shaft 34 may define a gentle curvature to present an atraumatic profile to the anatomy of the trachea TR. In some of these variations, the shaft 34 may have a radius of curvature SR of, e.g., 152.4 in., or ranging from, e.g., 12 in. to 300 in, such as shown in FIG. 2C. Additionally, the shaft may have a length SL (e.g., 7.85 in., or ranging from, e.g., 5 in. to 20 in.) to ensure that the distal engagement portion 38 may be advanced sufficiently from outside the patient's mouth M to a desired position within the trachea TR. Moreover, the shaft 34 may be sized to fit within the patient's trachea. TR even with the presence of ET tube ET, and may have a diameter that may range from, e.g., 0.16 in. to 1.2 in.

The shaft 34 may also define a receiving channel 36 along the length of the shaft 34 for positioning the inflation tube 12 along the length of the shaft 34 during advancement and delivery of inflatable member 14. In some variations, the receiving channel 36 may be configured to secure inflation tube 12 relative to the shaft 34. For example, the receiving channel 36 may be sized and configured to form a friction fit with the inflation tube 12 when the inflation tube 12 is positioned along the length of the shaft 34. In instances where the inflation tube 12 is tensioned relative to the shaft 34 (as described below), this tension may naturally position and hold the inflation tube 12 along the receiving channel 36. While shown in FIGS. 2A and 2B as being positioned on a surface of the shaft that is facing away from the center of curvature of the shaft 34, the receiving channel 36 may alternatively be positioned on a surface of the shaft facing toward the center of curvature of the shaft 34 or along a side surface of the shaft 34.

The receiving channel 36 may extend along shaft 34 to a port-receiving section 46 which comprises a port channel 48 for securement of the inflation port 16 coupled to inflation tube 12. Specifically, the port channel 48 may be sized and configured to receive and hold a portion of the inflation port 16. In some variations, the port channel 48 may be sized and configured to form a friction fit with the inflation port 16 when the inflation port 16 is positioned in the port channel 48. Additionally or alternatively, the port channel 48 may include on or more latches or covers (not shown) to hold the inflation port 16 in the port channel 48. The port receiving section 46 may also secure and align the inflation port 16 with the handle 32 such that a fluid reservoir, such as a syringe, may be inserted within a reservoir receiving channel 52 defined through the handle 32 and fluidly coupled to the inflation port 16 for passing a fluid or gas through the inflation tube 12 along the shaft 34 and to the inflatable member 14. The delivery instrument 30 may also incorporate a button or release 50 which may be optionally depressed to eject the inflation port 16 from the port channel 48 and the handle 30 (e.g. once the inflation port 16 has been fluidly decoupled from the fluid reservoir and/or inflation of the inflatable member 14 is completed).

While the inflatable member 14 may slide over or along the ET tube ET (e.g., prior to inflation of the inflatable member 14), the delivery instrument 30 may be removed from the ET tube ET once the inflatable member 14 has been desirably positioned. Thus, the distal engagement portion 38 may be configured to temporarily engage a portion of the cuff assembly 10 (e.g., the inflatable member 14). For example, in the variation shown in FIGS. 2A and 2B, the distal engagement portion 38 may be configured to have a cuff engagement member 40. The cuff engagement member 40 may be a partially or fully tubular member which extends distally from the shaft 34. The cuff engagement member 40 may also extend from the attachment with the shaft 34 peripherally away from the curvature of shaft 34 (i.e., away from the center of curvature of the shaft 34, such as shown in FIGS. 2A and 2B) or toward the curvature of the shaft 34 (i.e., toward the center of curvature of the shaft 34, such as will be described below with respect to FIGS. 8A and 8B). The cuff engagement member 40 may define an opening 44 sized and configured to slidingly receive an ET tube (e.g., the ET tube ET shown in FIG. 2A), such that the cuff engagement member 40 may temporarily attached to the ET tube, and may be advanced and/or retracted along the ET tube (which in turn may act as a guide for the cuff engagement member 40).

The distal end of the cuff engagement member 40 may be configured to temporarily engage the inflatable member 14. In some instances, the distal end of the cuff engagement member 40 may form an edge or lip that may engage the inflatable member 14. Additionally or alternatively, the cuff engagement member 40 may comprise one or more attachment mechanisms (such as pins, clips, etc.) that may engage the inflatable member 14. The engagement between the cuff engagement member 40 and the inflatable member 14 may allow the cuff engagement member 40 to advance the inflatable member 14 along the ET tube ET. Moreover, when the cuff engagement member 40 is a partially tubular member, the cuff engagement member 40 may be placed attached to (e.g., snapped on to) and/or removed from the ET tube ET anywhere along its length without having to be attached to or removed from the proximal end of the ET tube ET. When the cuff engagement member 40 includes a fully tubular member, the cuff engagement member 40 may be attached to or removed from the ET 15 tube ET over the proximal end of the ET tube ET. In some of these variations, the cuff engagement member 40 may comprise a frangible portion such that the fully tubular member may be broken or otherwise converted into a partially-tubular member, which may allow for removal of the cuff engagement member 40 anywhere along the length of the ET tube ET.

Additionally, the distal engagement portion 38 may comprise one or more elements to control or limit forward advancement of the cuff engagement member 40 (and the inflatable member 14 in instances when the cuff engagement member 40 advances the inflatable member 14). For example, in some instances it may be desirable to limit how far the inflatable member 14 may be advanced into the throat. In some variations, the distal engagement portion 38 may comprise a distal stop 42. The distal stop 42 may form a ledge or surface that may extend circumferentially along a proximal portion of the cuff engagement member 40 and/or the shaft 34. As shown in FIGS. 2A and 2B, the distal stop 42 may project away from the curvature of shaft 34 (e.g., away from the center of curvature of the shaft 34), although in other instances the distal stop 42 may extend toward the curvature of the shaft 34 (e.g., toward the center of curvature of the shaft 34). The distal stop 42 may engage one or more portions of the patient's anatomy during advancement of the distal engagement portion 38, which may halt or otherwise resist further advancement of the distal stop 42 (as described below).

The planar surface of the distal stop 42 may extend at any suitable angle relative to a longitudinal axis of the shaft 34. In some variations, the planar surface of the distal stop 42 may be transversely aligned relative to a longitudinal axis of the shaft 34. In other variations, the planar surface 42 may be aligned relative to the longitudinal axis of the shaft 34 at an angle less than 90 degrees. The opening 44 through the cuff engagement member 40 may also extend through the distal stop 42 for allowing the distal, engagement portion 38 to be placed on and removed from the ET tube ET anywhere along the length of the ET tube ET.

Figure 3A:
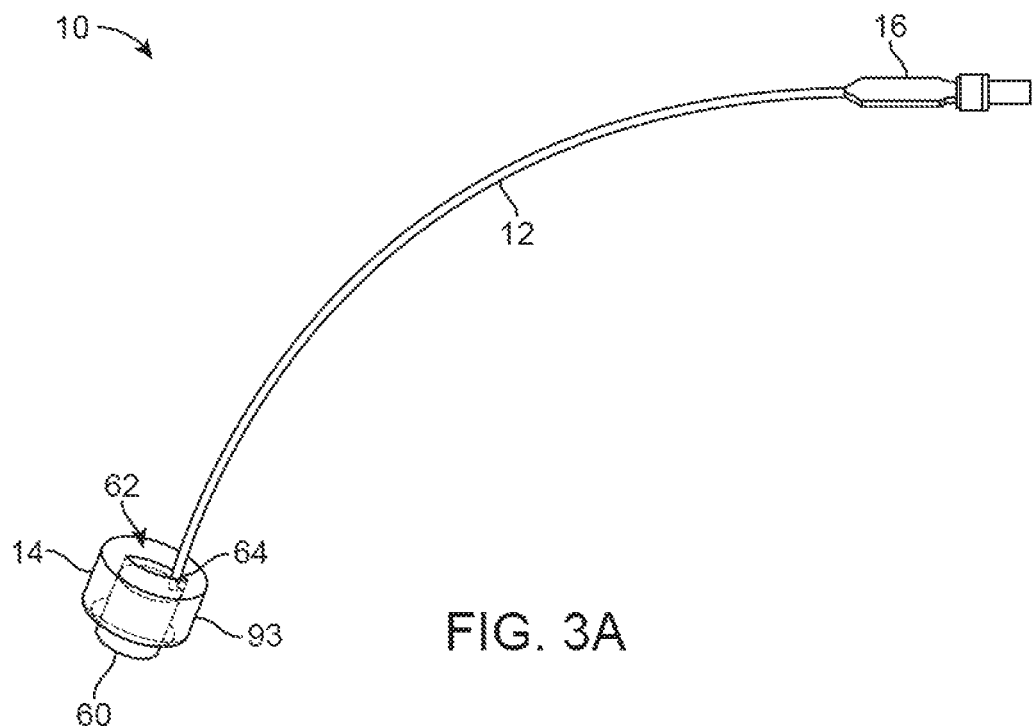
FIGS. 3A and 3B show perspective views of one variation of an inflatable cuff assembly.
Figure 3B:
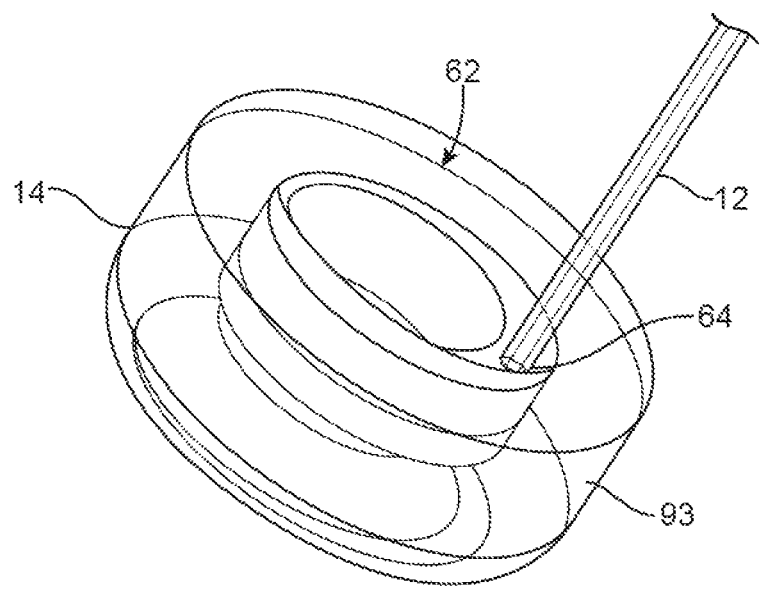

FIGS. 3A and 3B show perspective and detail perspective views of the cuff assembly 10 and inflatable member 14 removed from delivery instrument 30 to illustrate the details of the inflatable member 14. Because the inflatable member 14 may be inflated within the trachea TR, it may be comprised of a biocompatible polymeric material such as silicone, urethane, etc. or any number of suitable biocompatible materials and it may be appropriately sized in various dimensions depending upon the anatomy of the patient and the ET tube or laryngeal mask used for the patient. For instance, inflatable member 14 may be sized for pediatric or adult applications or even veterinary applications.

As shown in FIG. 3A, inflatable member 14 may comprise a balloon 93 supported by an inflation ring 60 which provides structural support for engagement with the delivery instrument 30 as well as for attachment to the balloon 93. The inflation ring 60 is generally sized to fit around an exterior portion of the ET tube ET yet still fit within the target tissue (e.g., the trachea). For example, the inflation ring 60 may have an outer diameter of, e.g., 13.5 mm, and an inner diameter of. e.g., 12.5 mm. The dimensions of the inflation ring 60 may be varied and may have any suitable length (e.g., about 15 mm). The inflation ring 60 may also provide an opening for fluidly coupling to inflation tube 12 via an inflation opening 64 which may have a diameter of, e.g., 1.5 mm, and may extend into the interior of the balloon 93. The inflatable member 14 itself may be configured to have a varied length such that the contact region between the inflatable member 14 and the trachea may range from a short circumferential point of contact to a lengthened contact region ranging from, e.g., 0.04 in. to 2.8 in. While shown in FIG. 3A as having a balloon 93 and an inflation ring 60, the inflation member 14 in some instances does not include an inflation, ring 60. In some of these variations, the inflation member 14 may comprise a balloon 93 that does not include an inflation ring. In these variations, a cuff assembly may include an inflation port and an inflation tube, wherein the inflation tube is connected to the balloon. In these variations, a cuff engagement portion of a delivery instrument may engage and advanced the balloon, such as described hereinthroughout.

Figure 3C:
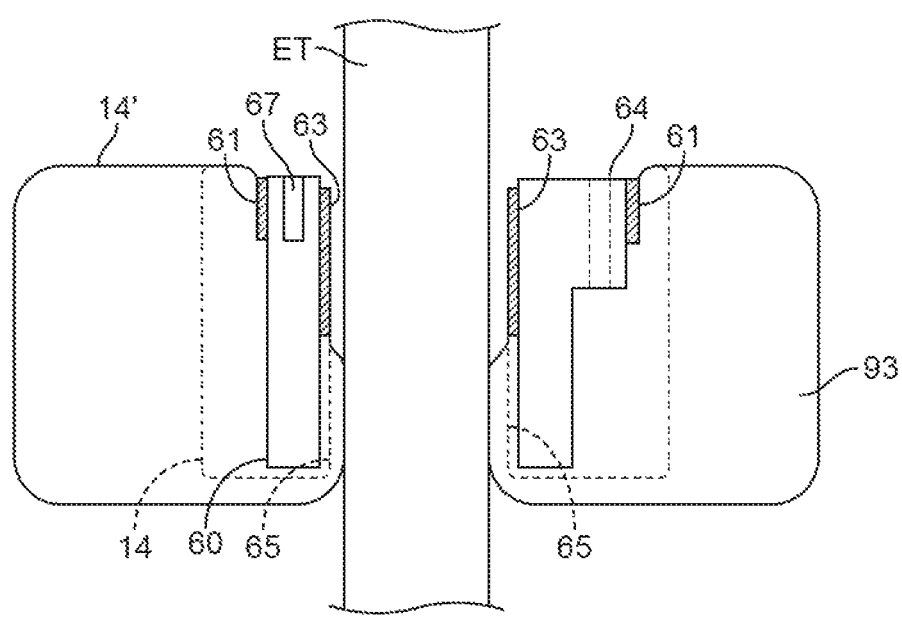
FIG. 3C shows a partial cross-sectional side view of an inflatable member illustrating the inflatable member expanded against the ET tube.

When an inflation member 14 comprises an inflation ring 60, the inflation ring 60 may be slid freely over or along an ET tube ET. Accordingly, the inflation ring 60 may not only allow for sufficient clearance between the ring interior and the exterior surface of the ET tube ET, but it may also provide for adequate sealing when the inflatable member 14 is expanded. FIG. 3C shows a partial cross-sectional side view of one variation where inflatable member 14' may have a balloon 93 attached to both exterior and interior surfaces of the inflation ring 60 to provide such a seal. A proximal portion of the balloon 93 may be attached along a proximal portion 61 of an exterior surface of the inflation ring 60 and the balloon 93 may be wrapped around a distal edge of the inflation ring 60 to be attached along a proximal portion 63 of an interior surface of the inflation ring 60, as shown. Hence, in its deflated state the inflatable member 14' may remain in a low profile with the balloon 93 positioned against the inflation ring 60 for delivery into the patient's airway. Once suitably positioned along the ET tube ET within the patient's trachea TR, the balloon 93 of the inflatable member 14' may be inflated via the inflation opening 64 to expand radially outward into contact against the tissue walls. Additionally, because a portion 65 of the balloon 93 of the inflatable member 14' along an inner surface of the inflation ring 60 is not attached to the inflation ring 60, this unattached portion 65 may also expand radially inward into contact against the outer surface of ET tube ET. This may seal the inflatable member 14' against the outer surface of the ET tube ET, which may provide complete sealing (e.g., sealing both against the tissue walls and the ET tube ET). As shown, an optional port 67 in the inflation ring 60 may allow for the connection of an optional tubing line, which may provide fluid communication external to the patient, for infusion or evacuation of additional agents into proximity of the inflatable member 14.

The compliant inflatable member 14 may be configured into various shapes beyond the toroidal configuration shown. For instance, an inflatable member 14 may alternatively be configured as a sphere, tube, cylinder, cube, ring, partial C-shaped ring, cone, corkscrew, or any other variation. Moreover, when the inflatable member comprises a balloon 93, the balloon 93 may have a wall thickness that may be uniform or varied and a surface that may be optionally smooth or textured to provide for additional securement against the tissue walls. The inflatable member 14 may be partially or completely filled with a gas (such as air, helium, nitrous oxide, etc.) or with any number of foams, gels, or other fluids (such as water, saline, etc.). Additionally, the inflatable member 14 may be coated or impregnated with any number of active agents such as an antibacterial, antibiotic, antiviral, antifungal, bacteriostatic or disinfectant substances (e.g. silver nitrate and chlorhexidine), etc. The inflatable member 14 may also be made from various materials, e.g., polyethylene terephthalate (PET), low-density polyethylene (LDPE), polyvinyl chloride (PVC), silicone, neoprene, polyisoprene, polyurethane (PU), etc.

Figure 3D:
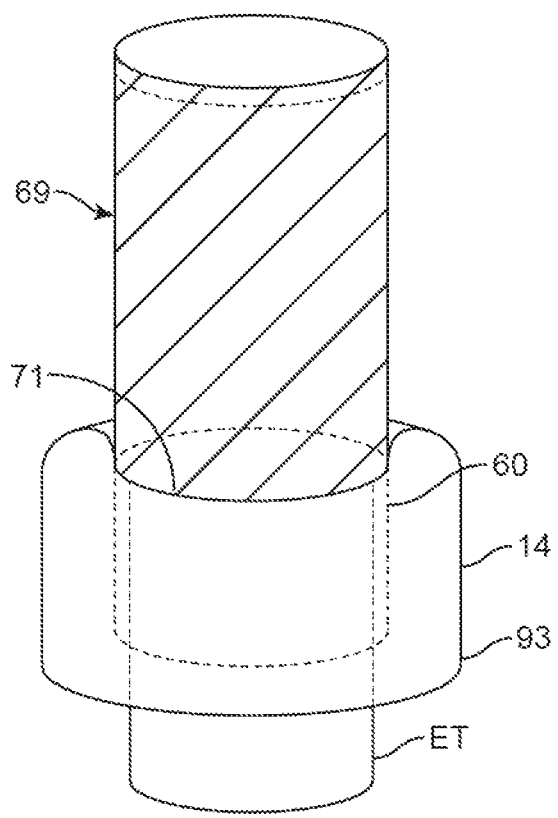
FIG. 3D shows a perspective view of another variation of an inflatable member incorporating a sealing sleeve.

In some variations, the cuff assembly 10 may comprise one or more sleeve members for sealing the cuff assembly 10 against the ET tube ET. For example, a variation of a portion of a cuff assembly is shown in the perspective view of FIG. 3D, which illustrates an example of an inflatable member 14 having a balloon 93 and an inflation ring 60, as well as a sealing sleeve 69 attached circumferentially to the inflatable member 14. For example, in some variations the sealing sleeve 69 may be attached to a top surface 71 of the inflation ring 60. The sealing sleeve 69 may generally comprise a tubular sleeve which may slide over ET tube ET as the inflation ring 60 is urged into position over the ET tube ET. Moreover, the sealing sleeve 69 may be comprised of an elastic or distensible material (such as a polymer or urethane), and the sealing sleeve 69 may be sized to have a diameter which is less than that of the inflation ring 60 (e.g., equal to or less than an outer diameter of the ET tube ET), such that the sealing sleeve 69 may conform closely to the ET tube ET outer surface and provide a seal between the inflatable member 14 and the ET tube ET.

Figure 4A:
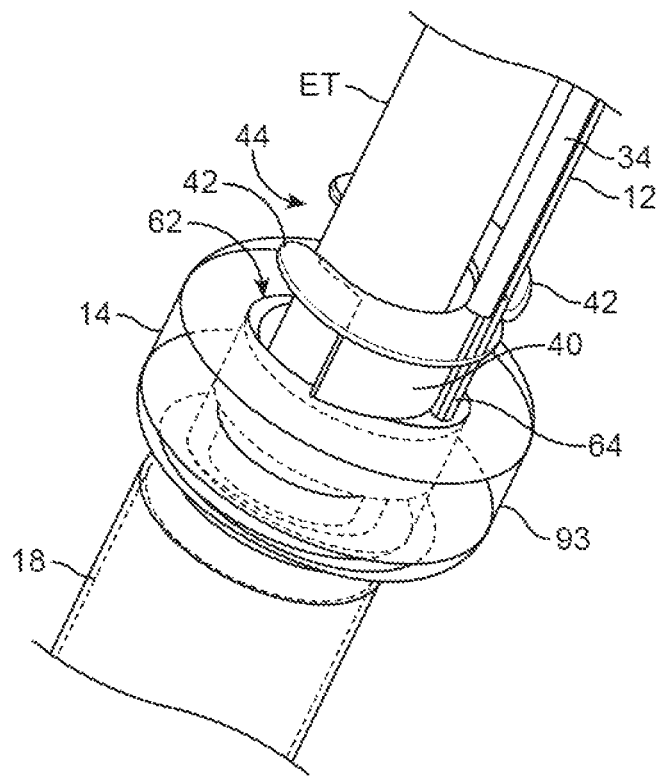
FIG. 4A shows a perspective view of a cuff assembly inflated and positioned via a deli very instrument along an ET tube.

As described above, in variations where the distal engagement portion 38 comprises a distal stop 42 forming a ledge or surface which extends circumferentially along a proximal portion of cuff engagement member 40, the distal stop 42 may guide and control the placement of the inflatable member 14 relative to the patient's vocal cords VC and the ET balloon 18. As shown in the perspective views of FIGS. 4A and 4B, the positioning of inflatable member 14 may be seen relative to the distal stop 42. Specifically, the inflatable member 14 may be positioned at a distal end of the cuff engagement member 40. Because the cuff engagement member 40 may extend distally from distal stop 42 by a distance (e.g., 2 mm to 1 cm), the inflatable member 14 may be spaced from the distal stop 42 by that distance. As the delivery instrument 30 is advanced along the ET tube ET within the patient, the inflatable member 14 may be pushed or urged distally (e.g., via the engagement with the distal end of the cuff engagement member 40) until the distal stop 42 bumps against the vocal cords VC. The distal stop 42 may have an outer diameter greater than that of the vocal cords VC such that the vocal cords VC may resist or otherwise prevent movement of the distal stop 42 beyond the vocal cords VC. The distal stop 42 and cuff engagement member 40 are preferably rounded to present atraumatic (or at least relatively low trauma) surfaces to the tissue, and the distal stop 42 may provide tactile feedback to the practitioner indicating that the distal stop 42 has reached the vocal cords VC. When the distal stop 42 has reached the vocal cords VC, the distance between the inflatable member 14 and the distal stop 42 (e.g., by virtue of the length of the cuff engagement member 40 distal to the distal stop 42) may position the inflatable member 14 distally beyond the vocal cords VC by that distance. In this way, advancing the distal stop 42 against the vocal cords VC may provide the practitioner with an indication that the inflatable member 14 has been positioned beyond and cleared the vocal cords VC (e.g., by the distance of the cuff engagement member 40) without requiring any direct visualization or imaging of the tissue or inflatable member. Hence, the inflatable member 14 may be positioned simply by positioning an opening 62 of the inflatable member 14 (e.g., which may be an opening of the inflation ring 60) around the ET tube ET and pushing the inflatable member 14 with the cuff engagement member 40 until the distal stop 42 abuts the vocal cords VC. This may automatically position inflatable member 14 a distance of anywhere from 0 to 7.5 cm below or inferior to the vocal cords VC (depending upon the length of the engagement member 40).

In some variations, the distal engagement portion 38 may comprise one or more atraumatic hook members sized and configured to selectively engage tissue to control forward movement of the distal engagement portion. FIG. 31A shows a perspective view of a distal portion of a variation of a delivery instrument 30' having a distal engagement portion 38' comprising hook members 110. The delivery instrument 30' may comprise a handle (not shown) and shaft 34, such as described above, and in some instances the shaft 34 may include a receiving channel 36. The distal engagement portion 38' may include a cuff engagement member 40 which may be positioned around an ET tube (not shown) and may advance one or more components of a cuff assembly (e.g., an inflatable member) along the ET tube.

The hook members 110 may extend from a proximal portion of the cuff engagement member 40 and may capture tissue between the hook members 110 and the cuff engagement member 40 (it should be appreciated that in some instances, one or more hook members 110 may extend from a portion of the shaft 34). For example, the hook members 110 may be sized and configured to receive a portion of the laryngeal inlet between the hook members 110 and the cuff engagement member 40. As shown in a perspective view in FIG. 3B, the cuff engagement member 40 may be positioned around an ET tube (not shown) and advanced along the ET tube until the hook members 110 capture the laryngeal inlet LI between the hook members 110 and the cuff engagement member 40. This engagement may resist additional forward movement of the distal engagement portion 38', and may position the cuff engagement member 40 at least partially in the trachea TR. When the cuff engagement member 40 is used to advance an inflatable member along the ET tube (as described above), catching the laryngeal inlet LI with the hook members 110 may position the inflatable member distally of the laryngeal inlet LI. Depending on the length of the cuff engagement member 40 distal of the hook members 110, the inflatable member may be positioned below the vocal cords (not shown). The hook members 110 are preferably round and blunt to reduce the likelihood of the hook members 110 damaging tissue during advancement. In some instances, the distal engagement portion 38' may comprise both one or more hook members and a distal stop.

In other alternatives, in addition to or as alternative of tactile feedback, other forms of feedback may be utilized such as an imaging device positioned along the shaft, inflatable member, ET tube, etc. (e.g., optical fibers, CCD imagers, CMOS imagers, etc.) or via a separate imaging instrument (e.g. a laryngoscope or endoscope). Additionally, other forms of feedback such as a fluid column which is raised as a distal stop abuts the vocal cords, pressure sensors, electrical impedance sensors, etc. may be used to provide an alert or indication to the user that the distal engagement portion is positioned at or near the target location (e.g., the vocal cords, laryngeal inlet, or the like).

In variations where the distal engagement portion comprises one or more hook members, the hook member may comprise one or more mechanisms to provide feedback as to the location of the distal engagement portion. For example, the delivery instrument may be configured to detect when the hook member captures tissue between the hook member and a cuff engagement member or shaft of the delivery instrument. The delivery instrument may be configured to form a connection between the hook member and the cuff engagement member or the shaft (e.g., a mechanical connection, a light-based connection, a magnetic connection, an electrical connection, combinations thereof and the like), and may be further configured to provide a feedback signal to an operator when the connection is broken or otherwise altered.

FIG. 31C shows a variation of the delivery instrument 30' as shown in FIGS. 31A and 31B, except that the distal engagement portion 38' comprises tether elements 112 extending between the hook members 110 and the cuff engagement member 40. One end of the tether element 112 may be fixed relative to the distal engagement portion 38' (e.g., to a tip of the hook member 110), while the other end may be attached to an indicator mechanism (not shown) that is configured to provide feedback (e.g., a visual or auditory signal) when tension is applied to the tether element 112. For example, the tether element 112 may be attached to a pressure sensor, and the delivery may be configured to generate a feedback signal to the operator when the pressure sensor measures a threshold tension applied to the tether 112. In these instances, the distal engagement portion 38' may be advanced until the tether element 112 engages tissue (e.g., the aryepiglottic fold of the laryngeal inlet LI). The tissue may resist further advancement of the distal engagement portion 38' and may thereby apply tension to the tether element 112, causing the indicator mechanism to provide a detectable signal to the operator. Additionally or alternatively, tension on the tether element 112 may cause the tether element 112 to break, and the indicator mechanism may be configured to detect breakage of the tether element 112.

Figure 4B:
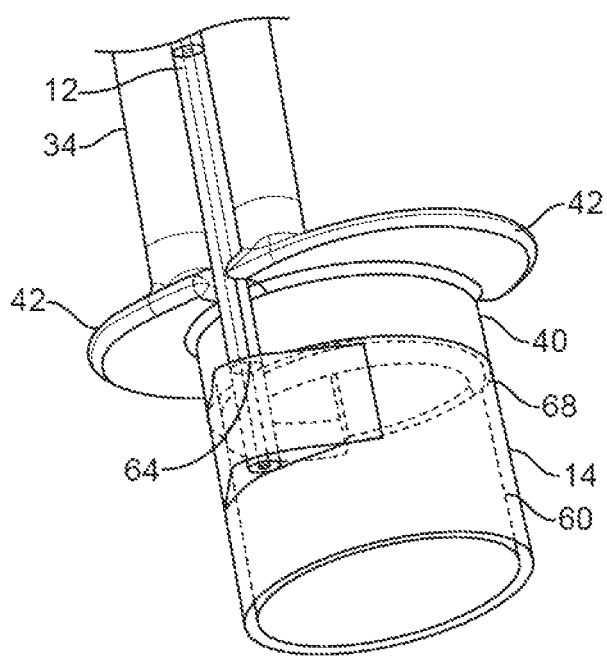
FIG. 4B shows a perspective view of another variation of a cuff assembly with an inflatable member in its deflated state.

As mentioned above, the cuff engagement member 40 may engage an inflatable member 14 in any suitable manner. For example, in some variations (such as shown in FIG. 4B) the distal edge of the cuff engagement member 40 may define a cuff engagement lip 68. This cuff engagement lip 68 may have a relatively smaller diameter than engagement member 40 such that engagement lip 68 may nestle or abut an inner edge of the inflatable member 14 (such as an inner edge of the inflation ring 60).

In some variations, the inflation, tube 12 may be configured to have a length shorter than the distance between the distal edge of the cuff engagement member 40 and the port channel 48 along the shaft 34 (e.g., between about 1 mm and about 10 mm shorter, or the like). In these variations, when the inflatable member 14 is positioned to engage the distal edge of the cuff engagement member 40, the inflation tube 12 may be stretched or otherwise tensioned along the shaft 34 to allow the inflation port 16 to be positioned in the port channel 48. This tension may pull and hold the inflation tube 12 along the shaft 34 in the receiving channel 36. The tension by the inflation tube 12 along the shaft 34 may also provide for a gentle proximally-directed force to the inflatable member 14 to help pull and secure the inflatable member 14 against the cuff engagement member 40. When the cuff engagement member 40 has a cuff engagement lip 68, the inflation ring 60 may be pulled and held in abutment with the cuff engagement lip 68 during advancement and positioning along the ET tube ET. To release the inflatable member 14 from the delivery instrument 30, the inflation port 16 and inflation tube 12 may be disengaged from the port-receiving portion section 46 and the shaft 34, respectively, and the delivery instrument 30 may be pulled proximally to disengage the distal engagement portion 38 from the inflatable member 14. The delivery instrument 30 may be disengaged either prior to, during, or after inflation of the inflatable member 14 to leave the inflatable member 14 positioned along the ET tube ET.

Alternatively, the attachment between the engagement member 40 and inflatable member 14 may comprise an elastic sleeve extending from the inflatable member 14 onto a tip of the cuff engagement member 40. Another alternative may comprise a mechanical fit, e.g., mechanical arms extending from the cuff engagement member 40 that may link to the inflation ring 60 and wherein rotation of the delivery instrument 30 could release the arms to disconnect the two from one another.

Figure 4C:
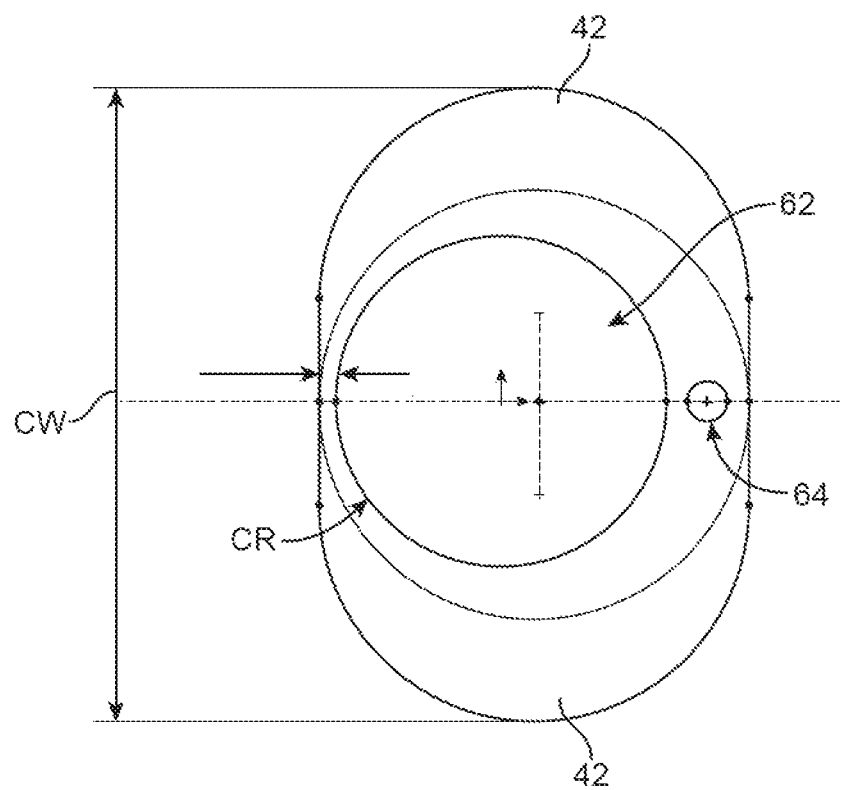
FIG. 4C shows a top view of one variation of a distal stop mechanism.

When the delivery instruments described here comprise a distal stop, the distal stop may have any suitable size and configuration. For example, FIG. 4C shows a top view of one variation of the distal stop 42 to illustrate exemplary dimensions for preventing passage of the distal stop 42 past the vocal cords VC. Thus, distal stop 42 may have a width CW of, e.g., 20 mm, and an opening 62 diameter CR of, e.g., 12.5 mm. The dimensions are intended to be illustrative and may varied depending upon the patient's anatomy, as well as the ET tube around which the distal stop may be placed. Additionally, while shown in FIG. 4C as fully surrounding the opening 62, the distal stop 42 may extend only partially around the opening 62.

Figure 4D:
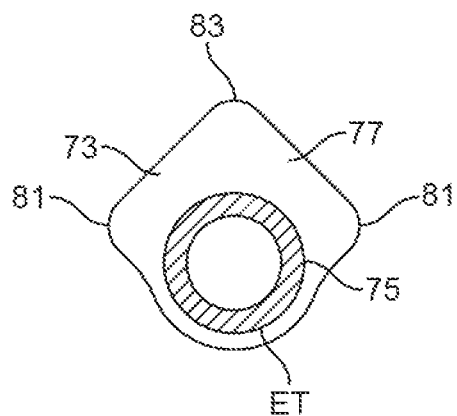
FIGS. 4D to 4F show top, side, and perspective views of another variation of a distal stop which may be configured to have a shape approximating a laryngeal inlet.

FIG. 4D shows a top view of yet another variation of a distal stop 73 which may be based on a shape of the vocal cords to more closely align with the anatomy and to ensure that the distal stop 73 is appropriately positioned relative to the vocal cords during deployment and positioning of the inflatable member 14. Hence, such a distal stop 73 may facilitate placement of the distal stop 73 proximal or superior to the vocal cords VC and also to the laryngeal inlet, e.g., upon the corniculate cartilages and cuneiform cartilages of the larynx. As shown, the distal stop 73 may be generally configured to circumferentially enclose about the ET tube ET through an opening 75 which enables the distal, stop 73 to be advanced or retracted for deployment. The distal stop 73 may flare radially outward to form apposed radially extended surfaces 81 which then taper to another radially extended surface 83 such that configuration mimics or generally conforms to the laryngeal inlet. Because of the differences in patient anatomy, the distal stop 73 may be fabricated in any number of sizes for use in different patients. Moreover, each of the surfaces 81, 83 may be rounded or curved to present an atraumatic surface to the tissue so as to reduce any trauma.

Figure 4E:
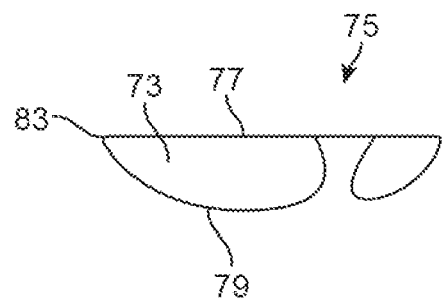
Figure 4F:
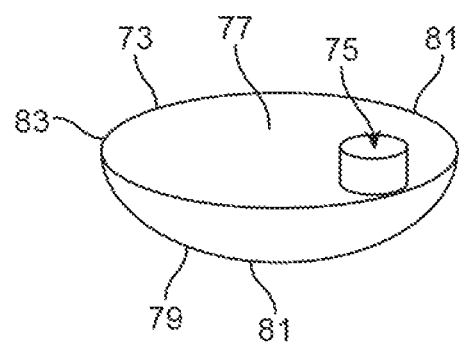

As shown in the partial cross-sectional side and perspective views of FIGS. 4E and 4F, the distal stop 73 may further define a top surface 77 which may be curved or flattened (as shown) as well as an apposed curved surface 79 which may present a smooth and curved surface to reduce any trauma to the contacted tissue during deployment and positioning.

This distal stop 73 as well as any of the stops described herein may be used in combination with any of the other features described. Hence, the distal stop 73 may be used in combination, e.g., with any of the inflatable member configurations as well as with any of the delivery instrument configurations.

Figure 32A:
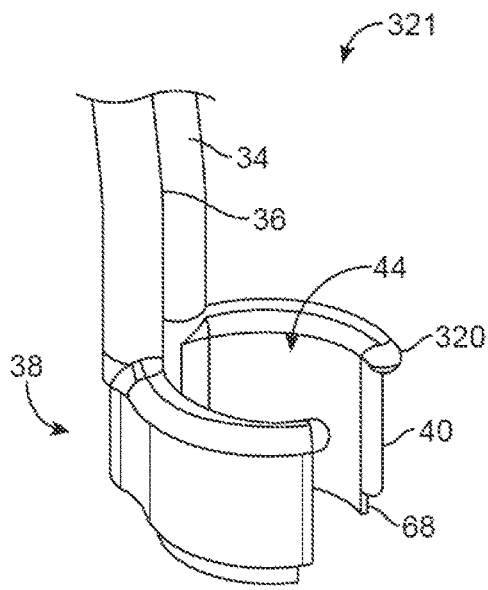
FIGS. 32A and 32B show front and rear perspective views of a variation of a delivery instrument having a distal stop.
Figure 32B:
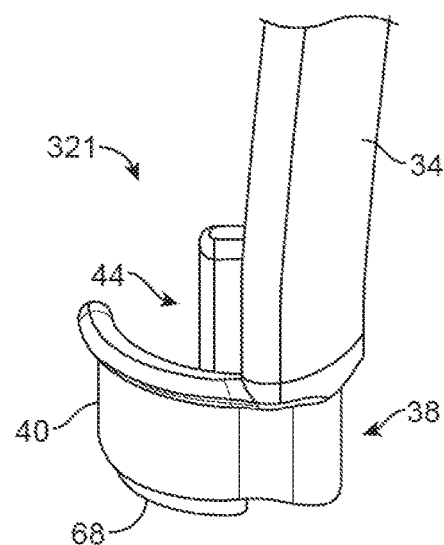

FIGS. 32A and 32B depict a front perspective view and a rear perspective view respectively of the distal portion of a variation of a delivery instrument 321 having a distal stop 320. As shown there, the delivery instrument 321 may comprise a shaft 34 and a distal engagement portion 38 such as described above. In some instances, the shaft 34 may include a receiving channel 36 for receiving an inflation tube of a cuff assembly (as shown in FIG. 32A, the receiving channel 36 may face away from the curvature of the shaft 34). Additionally, the delivery instrument 321 may comprise a cuff engagement member 40 (which in some instances may have a cuff engagement lip 68). The cuff engagement member 40 and distal stop 320 may extend away from the curvature of the shaft 34. As shown there, the distal stop 320 may have a diameter greater than that of the cuff engagement member 40 in order to allow the cuff engagement member 40 to advanced past tissue and for the distal stop 320 to engage tissue during advancement of the delivery instrument 321 (as described above), and may have rounded edges to help reduce tissue trauma.

Figure 34A:
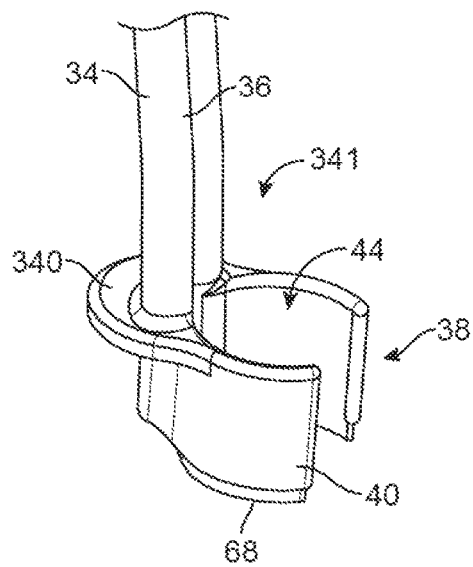
FIGS. 34A and 34B show front and rear perspective views of a variation of a delivery instrument having a distal stop.
Figure 34B:
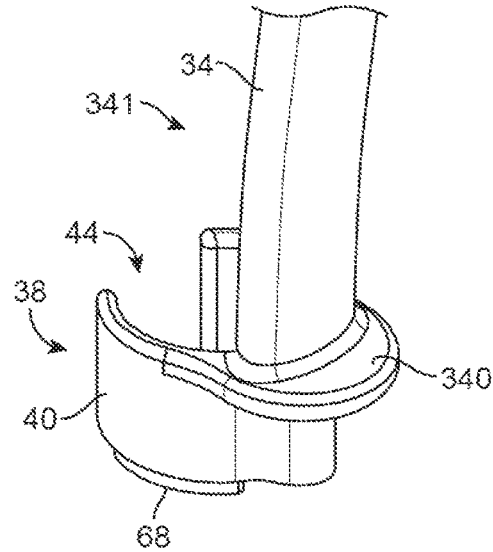

While both the cuff engagement member 40 and distal stop 320 extend away from the curvature of the shaft 34 in FIGS. 32A and 32B, it should be appreciated that one or more portions of a distal stop may extend toward the curvature of the shaft 34. For example, FIGS. 34A and 34B show front and rear perspective views, respectively, of the distal portion of a variation of a delivery instrument 341 having a distal stop 340. As shown there, the delivery instrument 341 may have a shaft 34 with a receiving channel 36 and a distal engagement portion 38 having a cuff engagement member 40 with a cuff engagement lip 68 such as described above. In this variation, the cuff engagement member 40 may extend away from the curvature of the shaft 34 while the distal stop 340 extends toward the curvature of the shaft 34 (or vice versa). In these variations, the distal stop 340 may be configured to engage or otherwise catch on tissue proximal or superior the vocal cords. For example, the distal stop 340 may be sized and configured to engage tissue of the laryngeal inlet (such as, for example, the corniculate cartilage and/or cuneiform cartilage of the larynx.

Figure 33A:
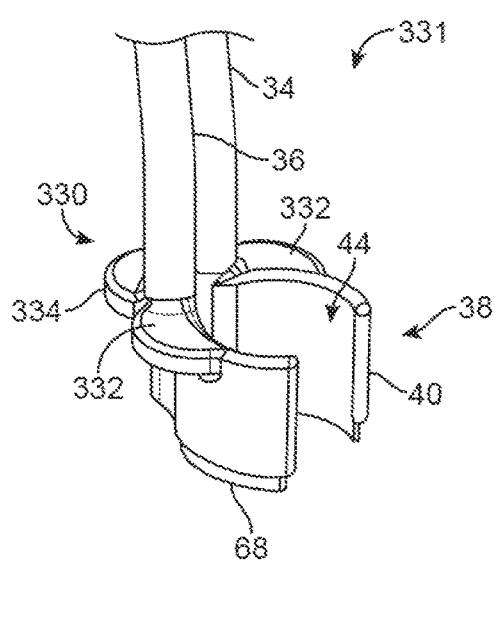
FIGS. 33A and 33B show front and rear perspective views of a variation of a delivery instrument having a distal stop.
Figure 33B:
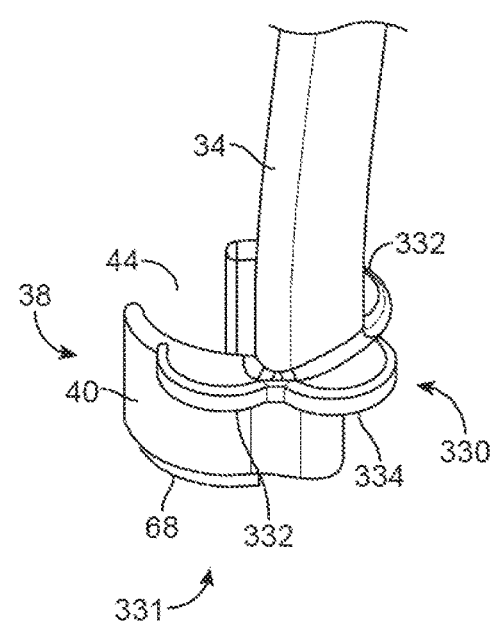

In still other variations, some portions of a distal stop may extend toward the curvature of the shaft while other portions of the distal stop may extend away from the curvature of the shaft. For example, FIGS. 33A and 33B show front and rear perspective views, respectively, of the distal portion of a variation of a delivery instrument 331 having a distal stop 330. As shown there, the delivery instrument 331 may have a shaft 34 with a receiving channel 36 and a distal engagement portion 38 having a cuff engagement member 40 with a cuff engagement lip 68 such as described above. In this variation, the cuff engagement member 40 may extend away from the curvature of the shaft 34, and the distal stop 330 may comprise a first lobe 334 extending toward the curvature of the shaft 34 and side lobes 332 extending away from the curvature of the shaft 34. Alternatively, the cuff engagement member 40 and side lobes 332 may extend toward the curvature of the shaft 34, while the first lobe 334 extends away from the curvature of the shaft 34.

Figure 4G:
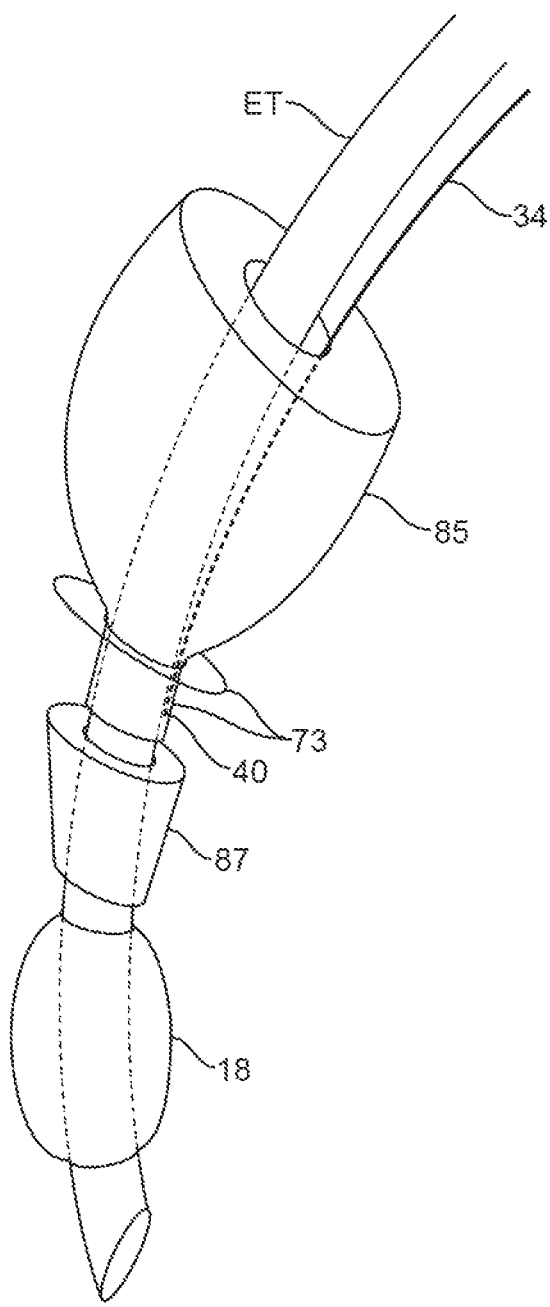
FIG. 4G shows an assembly view of an inflatable or expandable stop which may be used in combination with the distal stop.

In some variations, FIG. 4G shows an assembly view of an inflatable or expandable stop 85 which may be inflated or expanded prior to or during advancement of the inflatable member 14 (a tapered inflation ring 74 is depicted in FIG. 4G, although any suitable member as described here may be advanced) to limit forward advancement of the delivery instrument. The expandable stop 85 may be used in combination with any of the distal stops discussed above (depicted in FIG. 4G as distal stop 73 which may be formed with a circumferential opening to surround the ET tube ET, but in other instances may be an open member) to help prevent inadvertent advancement of the distal stop past the vocal cords. The inflatable or expandable stop 85 may be inflated with any number of fluids, foams, gels, scaffolds, etc. so as to be expanded for positioning, e.g., proximal or superior to the vocal cords VC in addition to the inflatable member 14 which may be positioned distal or inferior to the vocal cords VC.

Figure 35A:
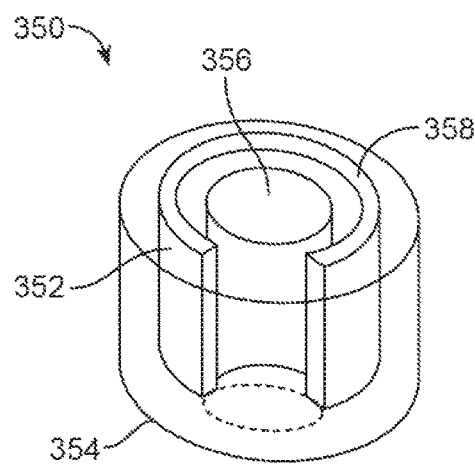
FIGS. 35A and 35B depict a perspective view and a top view of an inflatable member comprising an inflation ring.
Figure 35B:
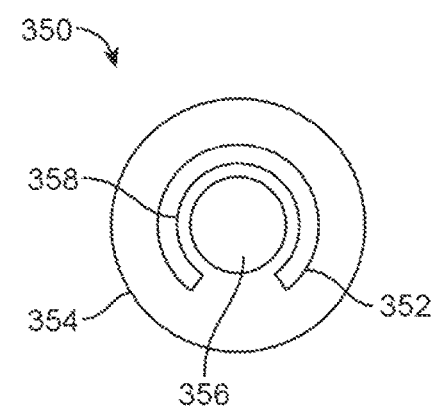

When an inflatable member 14 of the cuff assemblies described here comprises an inflation ring, the inflation ring may have any suitable size and shape. For example, while the variation of the inflation ring 60 shown in FIGS. 3A and 3B has a fully-tubular structure, in other variations an inflation ring may have a partially tubular structure. For example, FIGS. 35A and 35B show perspective and top views, respectively, of a variation of an inflatable member 350 comprising a partially-tubular inflation ring 352 and a balloon 354 attached thereto. A partially-tubular inflation ring 352 may reduce the overall profile of the inflatable member 350 when in a deflated configuration, which may facilitate advancement of the inflatable member 350 past tissue (e.g., through the vocal cords). As shown, the balloon 354 may define a tubular lumen 356. Alternatively, the balloon 354 may also be partially tubular. In some instances, the balloon may be bonded or otherwise attached to one or more portions of the inflation ring 352 (e.g., to an upper surface 358 of the inflation ring 352). The cross-sectional profile of the inflation ring 352 may be an arc subtending any suitable angle. In some variations, are may subtend an angle of at least 180 degrees. In some of these variations, the arc may subtend an angle of at least 270 degrees.

Figure 36A:
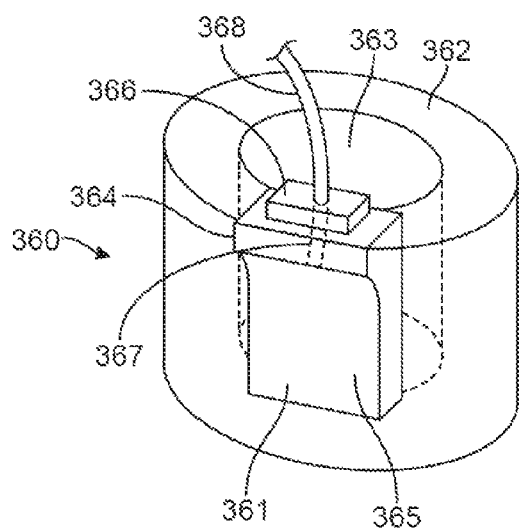
FIGS. 36A to 36C show a front perspective view, top view, and rear perspective view of components of an inflatable member comprising an inflation ring.

In other variations, an inflation ring may have a cross-section profile having an arc that subtends an angle of less than 180 degrees. In some of these variations, the arc may preferably subtend an angle of about 90 degrees or less, or more preferably may subtend an angle of about 45 degrees or less. FIG. 36A a shows a front perspective view of one such variation of an inflatable member 360 having an inflation ring 361 and a balloon 362 defining a lumen 363 therethrough. As shown there, the inflation ring 361 may extend partially around the lumen 363 (as shown there, the inflation ring 361 may extend less than 90 degrees around the lumen 363, and in some of these instances may extend 45 degrees or less around the lumen 363). The inflation ring 361 may comprise an upper segment 364 and a tapered lower segment 365. A tapered lower segment 365 may promote advancement of the inflation ring 361 past tissue by reducing the overall profile of the inflatable member 360. The inflation ring 361 may also comprise a tab portion 366 extending through the balloon 362 and an inflation opening 367 extending through the inflation ring 361 and into the interior of the balloon 362. An inflation tube 368 may be connected to inflation ring 361 and in fluid communication with the inflation opening 367 to allow for inflation of the balloon 362 therethrough.

Figure 36B:
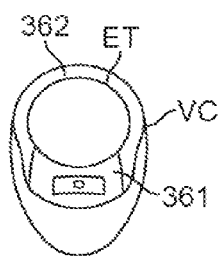

The reduced are length of the inflation ring 361 may reduce the overall profile of the inflatable member 360, and may facilitate introduction of the inflatable member 360 past tissue. For example, the opening between the vocal cords tends to be longer than it is wide. Accordingly, when the inflatable member 360 is advanced along an ET tube ET and past the vocal cords VC, as shown in a top view in FIG. 36B, the inflation ring 361 may be advanced through the open space between the vocal cords VC, which may reduce the resistance provided by the vocal cords VC against advancement of the inflatable member 360 therethough.

Figure 36C:
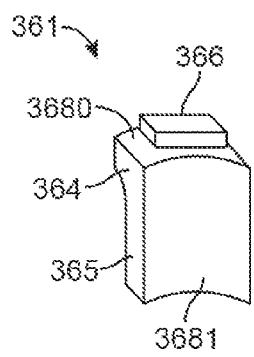

FIG. 36C shows a rear perspective view of the inflation ring 361 with the balloon 362 removed. In some instances, the balloon 362 may be bonded or otherwise attached to one or more surfaces of the inflation ring 361. For example, the balloon 362, when in a deflated configuration, may be bonded to an upper surface 3680 and a rear surface 3681 of the inflation ring 361. In some instances, the bonds may be configures such that the balloon 362 remains bonded to the upper surface 3680 during and after inflation of the balloon 362, but the bond between the balloon 362 and the rear surface 3681 may be broken during inflation of the balloon 362. Breaking the bond with the rear surface 3681 may facilitate the formation of a seal between the balloon 362 and the ET tube ET.

Figure 37:
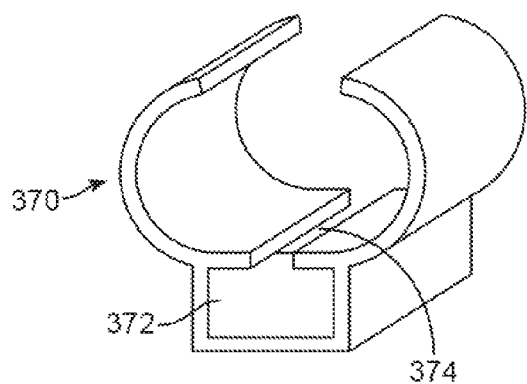
FIG. 37 shows a bottom perspective view of a variation of a cuff engagement member for use with the delivery instruments described here.

As mentioned above, the inflation ring 361 may comprise a tab 366 extending from the upper surface 368 of the inflation ring 361. In some instances, the tab 366 may be received within a portion of a delivery instrument to engage the inflation ring 361 with a delivery instrument. For example, FIG. 37 shows a variation of cuff engagement member 370 that may be used with any of the delivery instruments described above. As shown there, the cuff engagement member 370 may comprise a recess 372 sized to receive and engage the tab 366 of the inflation ring 361 of the inflatable member 360. In variations where the inflation tube 368 is tensioned (as described above), the inflation tube 368 may pull the tab 366 into the recess 372 and the upper surface 3680 of the inflation ring 361 against a distal portion of the cuff engagement member 370. The cuff engagement member 370 may be advanced along an ET Tube (not shown) to advance the inflatable member 360 along the ET tube. Also shown there is a receiving channel 374 for receiving a portion of the inflation tube 368.

In other variations, the inflation ring may include a recess in an upper surface of the inflation ring. For example, FIGS. 38A and 38B show a perspective view and a side view, respectively, of a variation of an inflation ring 381 which may be used with the inflatable members described here (such as inflatable member 360 described immediately above). As described above, the inflation ring 381 may have an upper portion 384 and a tapered lower portion 386, and an inflation opening 387 extending through the inflation ring 381 and into the balloon (not shown). The inflation ring 381 may also include a recess 388 in an upper surface 389 of the inflation ring 381, which may be configured to receive a portion of a delivery instrument to facilitate advancement of the inflatable member. For example, FIG. 39 shows a variation of cuff engagement member 390 that may be used with any of the delivery instruments described above. As shown there, the cuff engagement member 390 may comprise a tab 372 sized and configured to be received within the recess 388 of the inflation ring 381. In variations where an inflation tube (not shown) is tensioned to pull the inflatable device against the cuff engagement member 390 (such as described above), the inflation tube may pull the tab 392 into the recess 388 and the upper surface 389 of the inflation ring 381 against a distal portion of the cuff engagement member 390. The cuff engagement member 390 may be advanced along an ET Tube (not shown) to advance the inflatable member along the ET tube. Also shown there is a receiving channel 394 for receiving a portion of the inflation tube.

Figure 5A:
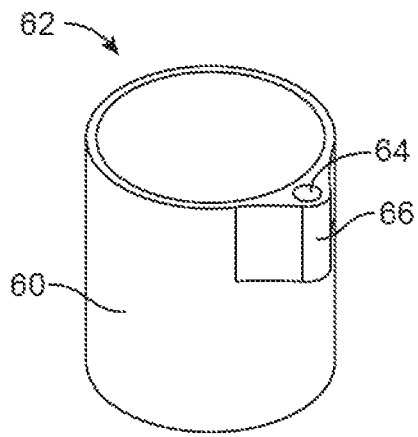
Figure 5B:
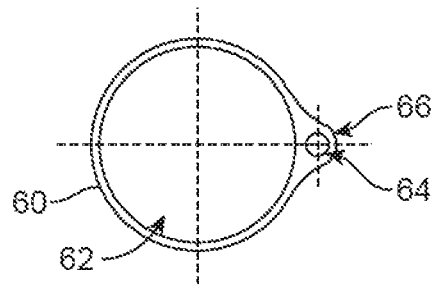
Figure 5C:
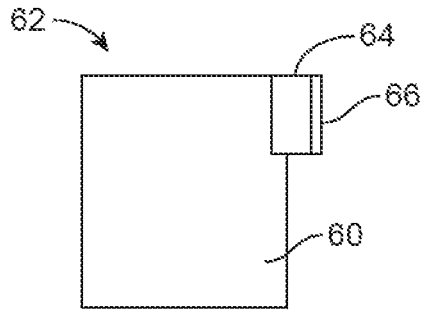

FIGS. 5A to 5C show perspective, top, and side views, respectively, of another variation of an inflation ring 60. In this variation, the inflation ring 60 may comprise a connection portion 66 which extends outwardly relative to an outer surface of the inflation ring 60. The connection portion 66 may define the inflation opening 64 therethrough for infusion of the gas or fluid into the balloon 93 of the inflatable member 14. Accordingly, an inflation tube (not shown) may be attached to the connection portion 66 (e.g., adhesive bonding, ultrasonic welding, or the like) such that the inflation tube may convey gas or fluid into the inflation opening 64.

Figure 5D:
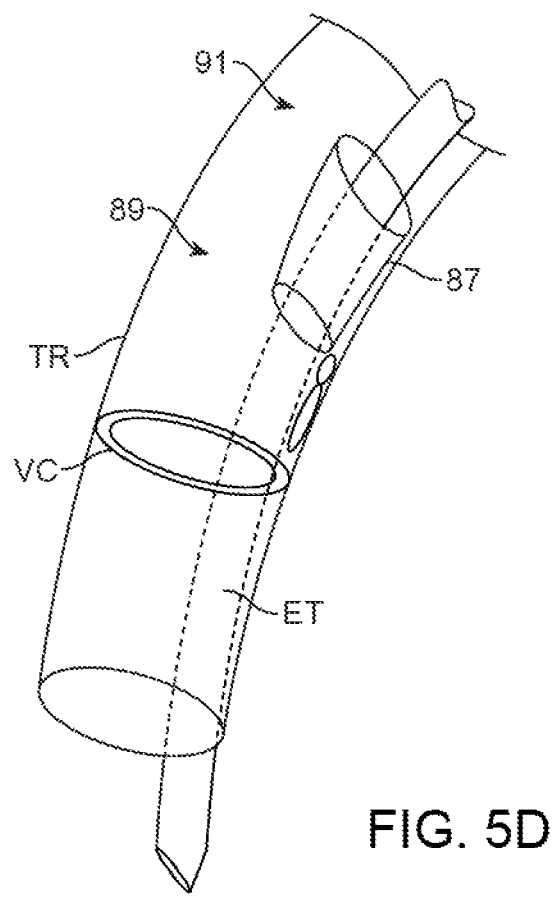
FIG. 5D shows a perspective view of an alternative inflation ring having a tapered surface.

Additionally, in the perspective view of FIG. 5D as well as in FIG. 4G above, an alternative inflation ring may be seen as having a tapered surface. The tapered inflation ring 87 may function similarly to the other inflation rings described herein but may also define a narrowed distal end 89 and an expanded proximal end 91 which may facilitate passage of the ring 87 past the laryngeal inlet which is the opening connecting the pharynx and the larynx as well as past the vocal cords VC during positioning of the inflatable member 14. In yet other alternatives, the inflation ring 87 may be tapered along both proximal and distal ends as shown in the variation of FIG. 5E. As illustrated, the distal end 89 may be tapered as well as the proximal end 89' such that the expanded middle portion 91 is positioned between each narrowed end 89, 89'. Such a configuration may facilitate not only the insertion of the ring 87 past the laryngeal inlet and the vocal cords VC but may also facilitate its removal as well for removal from the patient's body or for repositioning.

While discussed above as including an inflatable member 14, the cuff assemblies described here may comprise other variations of barriers, which in some instances may be delivered using one or more of the delivery instruments described here. FIGS. 6A and 6B show perspective views of another variation where a cuff assembly 70 may optionally incorporate a flared distal portion which extends into a reconfigurable member 72 (optionally an inflatable member). The reconfigurable member 72 may be flexed into an inverted member 72' to facilitate drainage of any fluids or debris which may have pooled above the member 72. The member 72 may be inverted manually or on a timed schedule by various mechanisms if so desired.

Figure 7A:
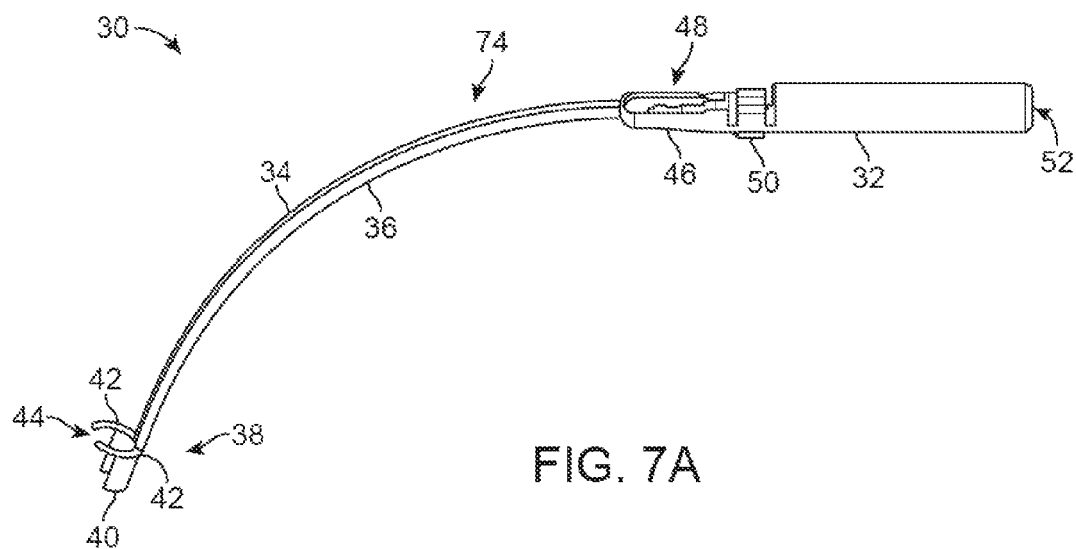
FIGS. 7A and 7B show perspective and detail views of one variation of a delivery instrument.
Figure 7B:
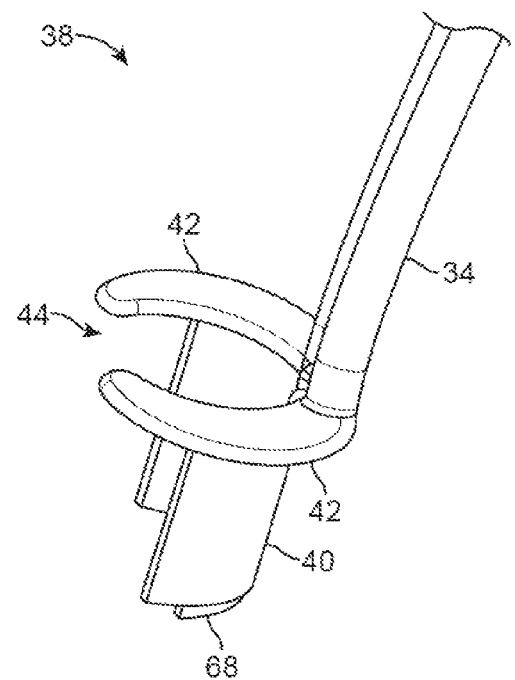

FIGS. 7A and 7B show perspective and detail perspective views of the delivery instrument 30 without the cuff assembly 10 for clarity. As shown, the distal stop 42 may extend circumferentially away from a curvature of shaft 36 to form an open member which defines opening 44 for receiving the ET tube ET. Also shown are engagement member 40 and engagement lip 68 also extending distally to form a partial tubular structure which is also opened for receiving the ET tube ET. Aside from the length of engagement member 40 as guiding placement of the inflatable member 14 relative to a position of stop 42 and the vocal cords VC, another variation may utilize graduations 74 or other markers defined along the shaft 36 or handle 32 to measure the distance from a first point along the ET tube ET relative to a second point to facilitate positioning of the inflatable member 14. For example, the delivery instrument 30 may be advanced along the ET tube ET until a first marking on the delivery instrument is aligned with one or more markings on the ET tube ET. Additionally or alternatively, the delivery instrument 30 may be advanced along the ET tube ET until a marking on the delivery instrument reaches one or more anatomical landmarks (e.g., the teeth of the patient). This may provide an indication that the deli very instrument 30 has been advanced far enough to have properly position the cuff assembly. In each of the variations described, the mechanisms to facilitate positioning of the inflatable member may be utilized in any number of combinations as practicable.

Figure 8A:
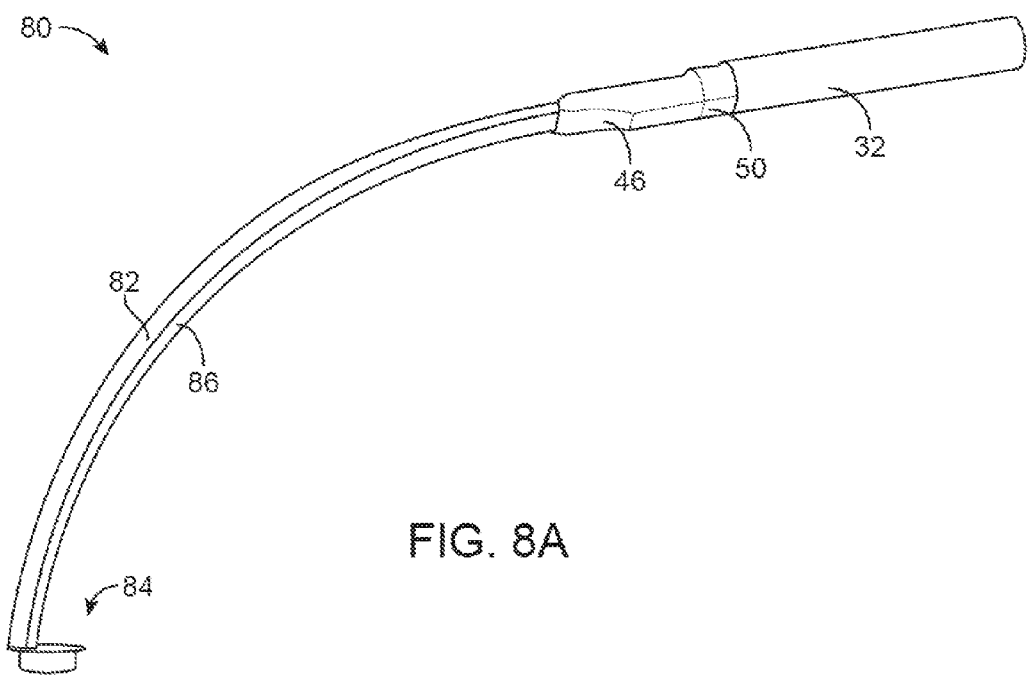
FIGS. 8A and 8B show perspective and detail views of another variation of a delivery instrument.
Figure 8B:
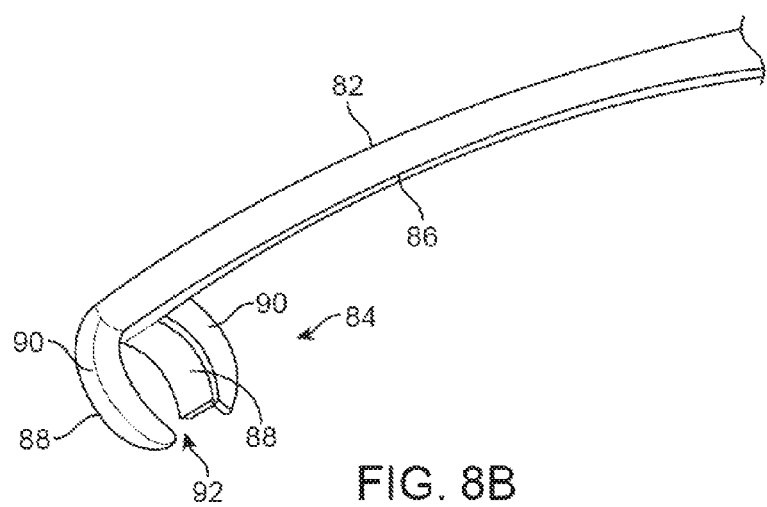

Another variation of the delivery instrument 80 is shown in the side and perspective views of FIGS. 8A and 8B which illustrate the arcuate or curved shaft 82 extending from the handle 32. The shaft 82 may have the same or similar dimensions as the previous variation and may likewise define a lumen receiving channel 86 along the shaft 82. However, in this variation, the distal engagement portion 84 may have a distal stop 90 that extends toward the curvature of shaft 82 rather than outwardly such that opening 92 is open towards the curvature of shaft 82 as well for receiving ET tube ET. Similarly, the cuff engagement member 88 may extend distally from distal stop 90 for engagement with inflatable member 14.

Figure 9A:
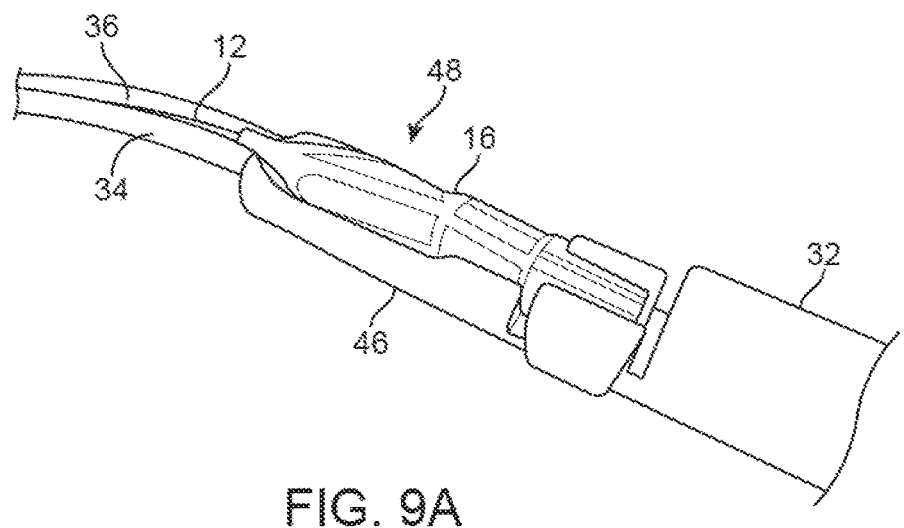
FIGS. 9A to 9C show detail perspective views of the delivery instrument and a portion of a cuff assembly.
Figure 9B:
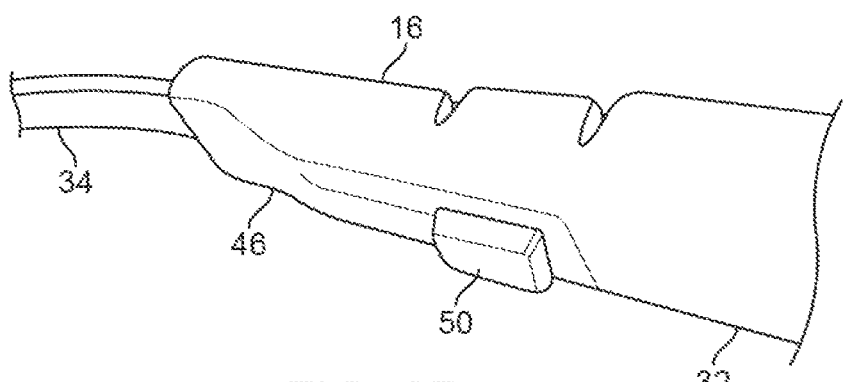
Figure 9C:
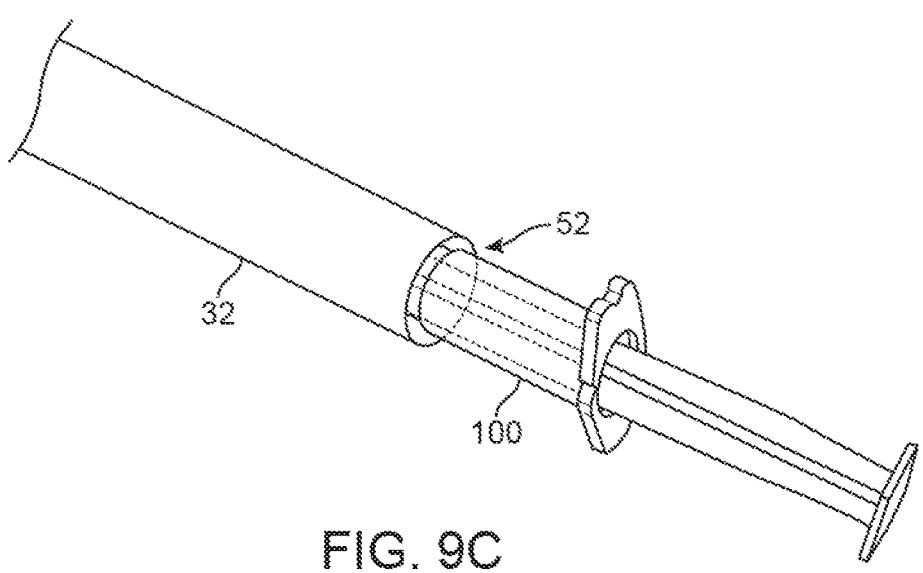

Regardless of which direction the distal engagement portion extends, securement of the inflation port 16 along the port receiving section 46 within channel 48 may be accomplished in the same manner. One variation is shown in the perspective views of FIGS. 9A to 9C which illustrate port 16 positioned securely within the port channel 48 and the inflation tube 12 positioned in the receiving channel 36. Placement within channel 48 may align the inflation port 16 with the handle 32 for fluidly coupling with an inflation fluid reservoir 100, e.g., syringe, which may be inserted within a reservoir receiving channel 52. Once the inflation port 16 is to be removed or detached from delivery instrument 30, a button or release 50 (shown as a projection extending from handle 32 attached along the port-receiving section 46) may be actuated to push or eject the injection port 16 after it has been decoupled from the fluid reservoir 100.

Figure 11A:
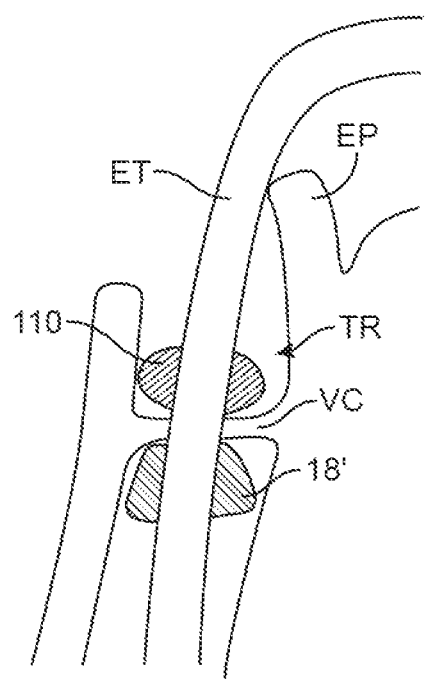
FIGS. 11A and 11B show side views of additional variations of a cuff assembly.

When cuff assembly 10 comprises an inflatable member, the inflatable member 14 may be shaped into any number of suitable configurations. FIG. 11A shows another example where the inflatable member may be configured as an inversely tapered balloon 110 such that the balloon 110 tapers and narrows towards the vocal cords VC when in position. In this case, the balloon 110 may be advanced over the ET tube ET and positioned above or superior to the vocal cords VC. The corresponding ET balloon 18' may also be optionally tapered to narrow towards the vocal cords VC as well, if so desired. Such a configuration may ensure that inflation of the balloon 110 does not damage the vocal cords VC.

Figure 11B:
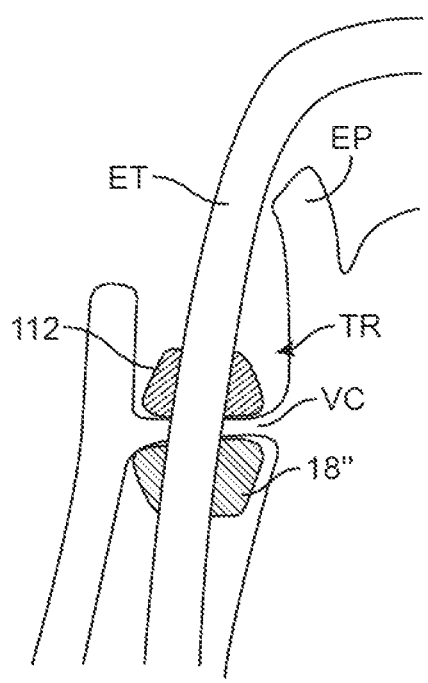

FIG. 11B shows yet another variation where the balloon 112 may be tapered to narrow away from the vocal cords VC when advanced over the ET tube ET to be positioned above or superior to the vocal cords VC. Optionally, the ET balloon 18" may also be tapered in a similar manner to narrow away from the vocal cords VC.

Another variation of the balloon is shown in the top views of FIGS. 12A and 12B which illustrate an inflatable member 122 which may be wrapped about itself in a low-profile for delivery but when inflated via inflation tube 120, member 122 may unwind within the trachea TR in a direction opposite to the wrapped direction to then wrap around the ET tube ET. FIGS. 13A to 13C show perspective views of yet another variation of a balloon 124 which may be similarly wrapped about itself and which may unwind in the same direction as the direction of the wrapped direction when inflated for securement around the ET tube ET.

Aside from utilizing a single inflatable member, multiple inflatable members may be used as an alternative balloon. Another variation is shown in the perspective and side views of FIGS. 14A and 14B which illustrate how multiple inflatable members, such as a first C-shaped balloon 130 which defines an opening 132 and a second C-shaped balloon 134 which similarly defines an opening 136 may be aligned along a centerline 138 such that the openings 132, 136 are off-set. With the first and second balloons 132, 134 inflated and stacked upon one another in their off set configuration, as shown in the side view of FIG. 14B, a sufficient seal may be formed by the balloons.

Figure 15A:
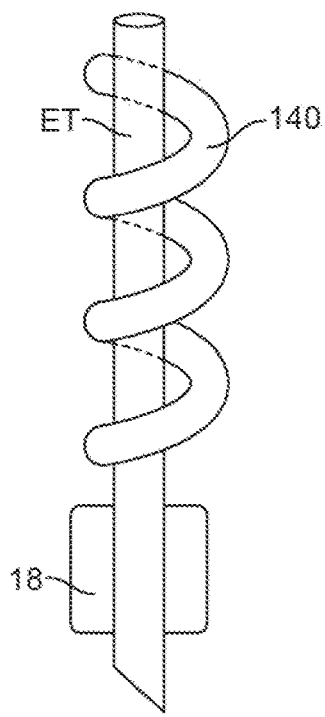
FIGS. 15A and 15B show side views of yet another variation of a balloon configured into a collapsible helical shape.
Figure 15B:
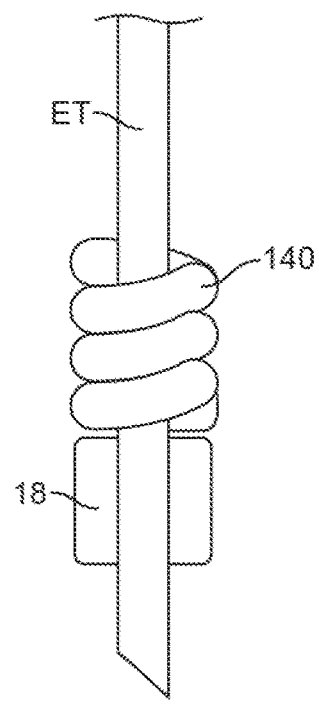

Yet another variation is shown in the side views of FIGS. 15A and 15B which illustrate a helically-shaped balloon 140 which may be advanced in an elongated configuration along ET tube ET during delivery. Once suitably positioned, the balloon 140 may be collapsed upon itself and/or inflated to form a composite seal around ET tube ET, as shown in FIG. 15B.

Figure 16A:
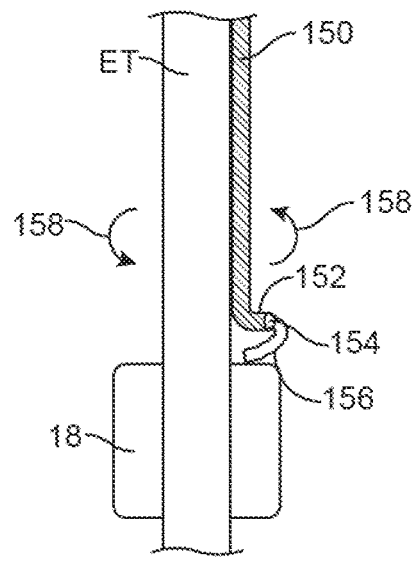
FIGS. 16A to 16C show side views of yet another variation of a balloon configured into a deployable expandable member via a rotating lumen.
Figure 16B:
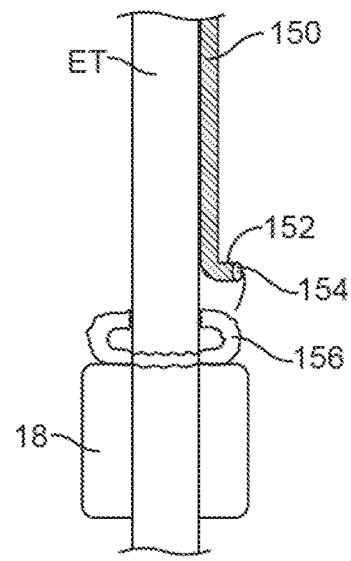
Figure 16C:
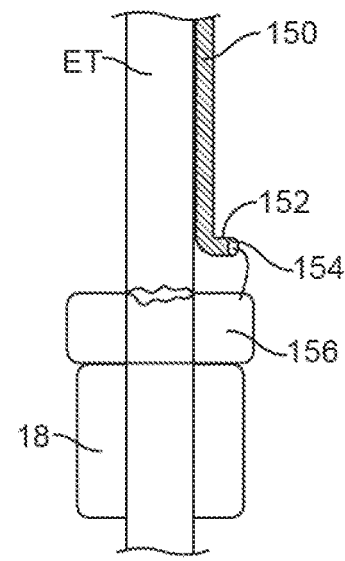

In yet another variation, FIGS. 16A to 16C show a variation where an inflation tube 150 may be advanced along or over ET tube ET such that an angled portion 152 defining an opening 154 may be positioned in proximity to either the vocal cords VC or FT balloon 18, as shown in FIG. 16A. An inflatable member 156 or expandable material may be introduced through the opening 154 and the inflation tube 150 may be actuated or rotated about the ET tube ET, as indicated by the direction of rotation 158, as shown, in FIG. 16B, such that the opening 154 may introduce the member 156 (or expandable material) entirely around the circumference of the ET balloon 18. The deposited member 156 may be subsequently inflated to form the seal against the vocal cords VC or ET balloon 18 as shown in FIG. 16C.

Figure 17A:
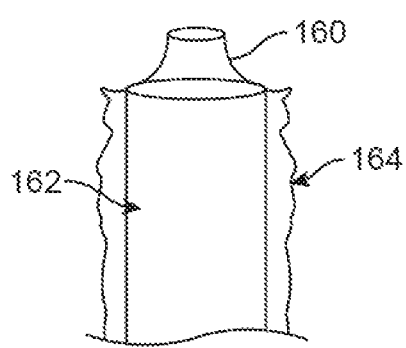
FIGS. 17A and 17B show side views of yet another variation of a balloon configured as an expandable sheath.
Figure 17B:
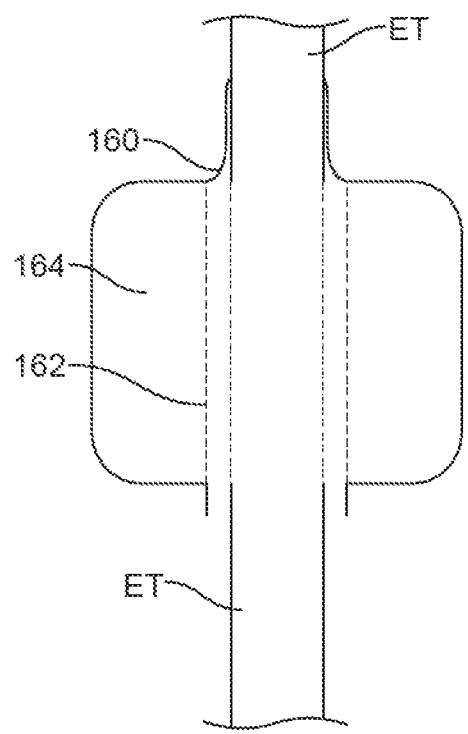

Another variation of the balloon may be seen in the side views of FIGS. 17A and 17B which illustrate a lumen 160 which forms a sheath 162. An inflatable member 164 may be formed or attached around an exterior of the sheath 162 such that the sheath 162 may be advanced over or along the ET tube ET and appropriate positioned. Once positioned, the inflatable member 164 may be inflated or expanded to form the seal around the ET tube ET. The lumen 160 may also form a seal around the ET tube ET to prevent the passage of debris or fluids between the sheath 162 and ET tube ET.

Figure 18A:
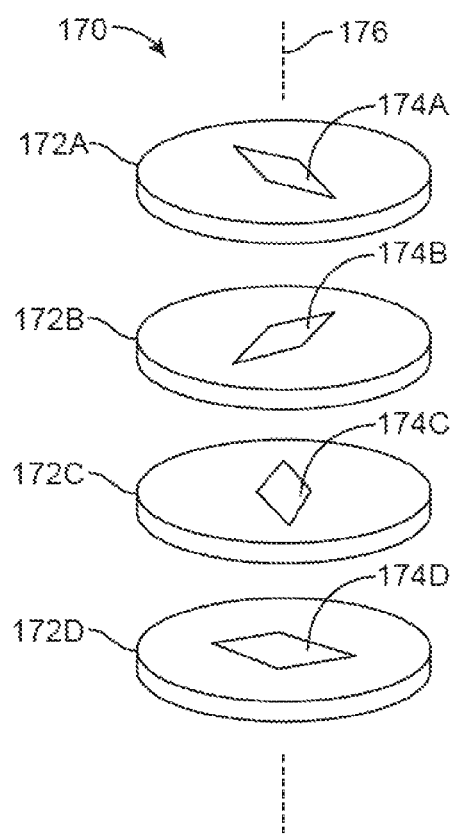
FIGS. 18A and 18B show perspective and side views of another variation where several discs may be stacked upon one another in an off-set manner may be used obstruct the opening of the trachea.
Figure 18B:
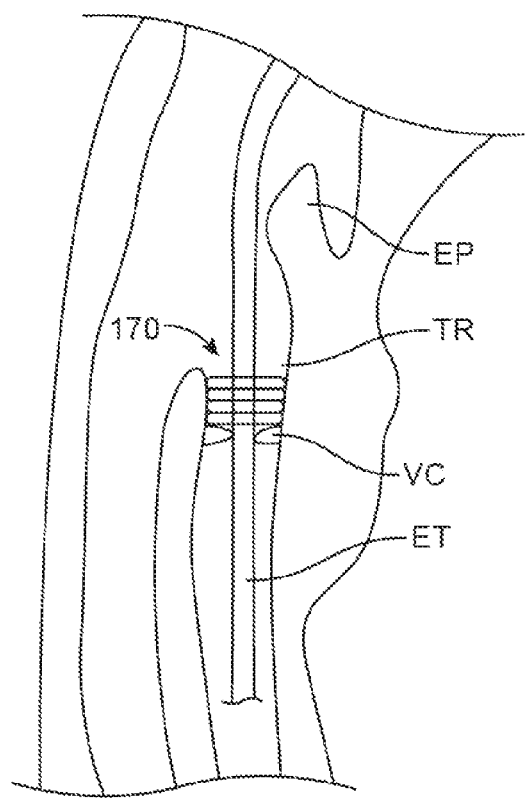

Yet another variation is shown in the perspective and side views of FIGS. 18A and 18B which illustrate a one or more discs 172A, 172B, 172C, 1720 each having a respective trapezoidal opening 174A, 1748, 174C, 174D that when stacked along a longitudinal centerline 176 as a disc assembly 170 in staggered manner may create a seal. Each of the discs may be formed from any number of biocompatible compliant materials such as silicone. Although four discs are illustrated, as few as two or more than four discs may be utilized. The opening in the center of the discs may allow them to be slid down the ET tube ET and placed adjacent to the vocal cords VC. Moreover, the one or more discs may be used with the ET tube ET or in combination with the cuff assembly 10 as well.

In this variation and in each of the variations described, the cuff assembly 10 may be utilized in any number of combinations as practicable. For example, the cuff assembly 10 and delivery instrument 30 may be utilized with any of the variations described in FIGS. 12A to 18B in any number of combinations.

Aside from the use of inflatable members or stacked discs, the cuff assembly 10 may also be utilized in combination with one or more biocompatible, hydrophilic or hydrophobic materials such as gel, polymer, poloxamer, foam, solid, etc. along with an ET tube ET. Such a substance could change state between solid, gel, liquid or vapor depending upon various factors such as temperature, pH, humidity, or could be triggered by external mechanisms such as electrical current, chemical reaction with a substrate, interaction with another substance such as an endotracheal tube or balloon coating. The substance may also be impregnated with various active agents such as antibacterial, antibiotic, antiviral, antifungal, bacteriostatic, or disinfectant substances in order to diffuse local.

Figure 19:
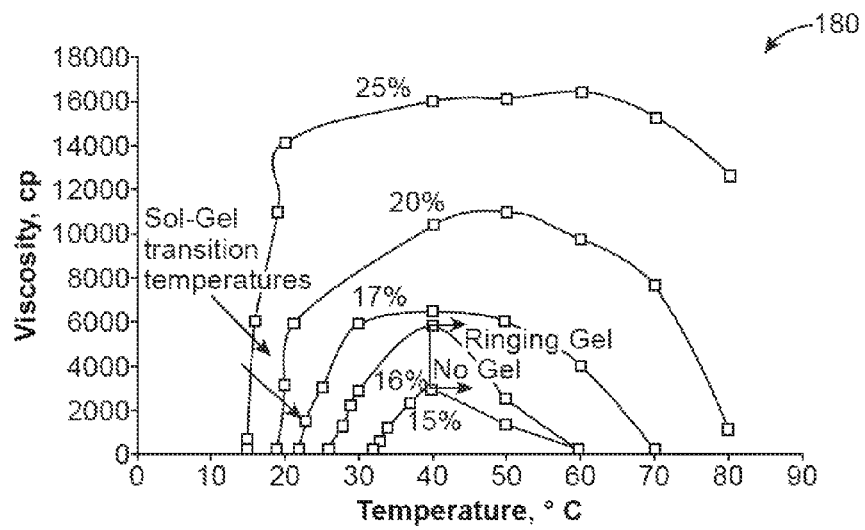
FIG. 19 illustrates a chart detailing the temperature vs. viscosity of a thermosensitive composition which may be infused in combination with a balloon or other inflatable member.

One variation may include a composition comprised of a purified inverse thermosensitive polymer that is liquid or aqueous at ambient temperature but turns into a solid elastic state at body temperature, conforming to the trachea or larynx to create a seal. One variation may utilize poloxamers which exhibit surfactant properties with extremely low toxicity and immunogenic responses. A chart 180 of temperature vs. viscosity is shown in FIG. 19 to illustrate one such material which may be used such as Pluronic, polymers (BASF Co., NJ).

Figures 20A, 20B, 20C:
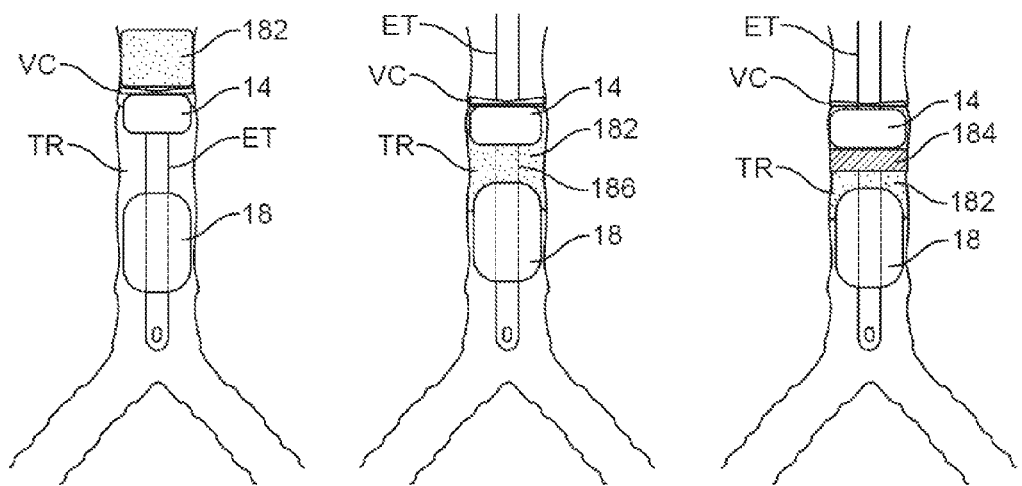
FIGS. 20A to 20C show side views of a cuff assembly used in combination with a thermosensitive composition.

Such a material may be used to supplement use of the inflatable member 14 by infusing the substance 182, e.g., above or superior to the vocal cords VC once the ET balloon 18 and inflatable member 14 have been deployed, as shown in FIG. 20A. Alternatively, the substance 182 may be infused in the space below or inferior to the vocal cords VC between the inflatable member 14 and ET balloon 18, as shown in FIG. 20B. In yet another alternative, a second infused material 184 having second viscosity may be infused atop the substance 182 in the space between the inflatable member 14 and FT balloon 18, as shown in FIG. 20C. Alternatively, the dual-layered material may be infused above the vocal cords VC as well. The dual-layered material, such as a dual-layered polymer gel, may each have compositions which solidify at different temperatures. For instance, the substance 182 may be injected or infused first to create a base for the second layer 184. Once the substance 182 has solidified, the second layer 184 may be injected or infused.

Another variation may include a purified inverse thermosensitive polymer which is configured to remain a liquid at body temperature and solid when cooled. The region around the polymer may be cooled to keep the polymer solid during use via a cooling device introduced either through the ET tube ET or embedded along an outer surface.

Figure 21:
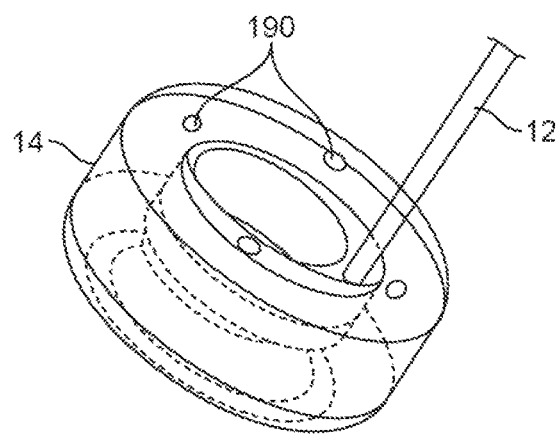
FIG. 21 shows a perspective view of a balloon defining one or more openings for the infusion and/or evacuation of a composition.
Figure 22:
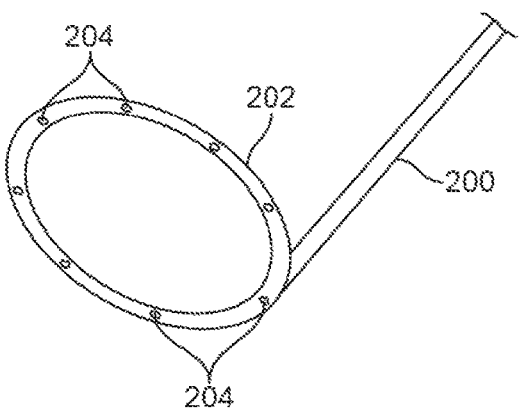
FIG. 22 shows a perspective view of an infusion and/or evacuation instrument for infusing a composition into proximity to a balloon.

To facilitate the delivery and infusion of the substance (as well as the removal), one or more openings 186 may be defined, e.g., along the ET tube ET itself (as shown in FIG. 20B). Alternatively, one or more openings 190 may be defined along the inflatable member 14, as shown in the perspective view of FIG. 21, where the openings 190 are fluidly coupled through a separate lumen to a source or pump external to the patient. Another variation is shown in FIG. 22 which illustrates a separate instrument having an infusion lumen 200 and an infusion ring 202 which defines one or more infusion openings 204. The infusion lumen 200 may be advanced separately from (or simultaneously with) the cuff assembly 10 around the ET tube ET. Once the material has been infused, the infusion lumen 200 may be removed. Similarly, once the material is to be removed, the infusion lumen 200 may be introduced into the body and used to suction out the material.

Figure 23A:
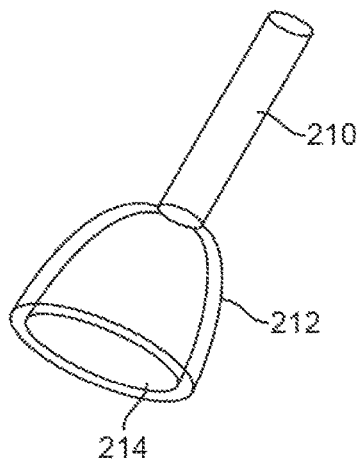
FIGS. 23A and 23B show perspective views of additional variations for instruments for infusing and/or evacuating a composition.
Figure 23B:
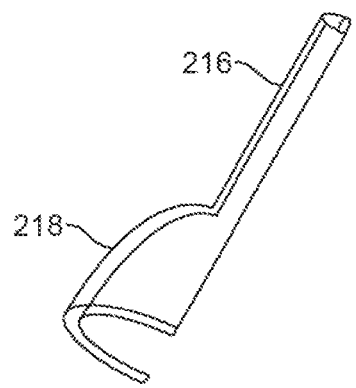

Alternative variations for instruments which may be used to introduce or remove the substances are shown in the perspective views of FIGS. 23A and 23B. FIG. 23A illustrates a sheath 210 which has a conical infusion member 212 which defines an opening 214. Sheath 210 may be advanced over or along the ET tube ET separately from or simultaneously with the cuff assembly 10 to infuse (or suction out) the substances. Similarly, support attachment member 216 may be clipped onto a portion of the ET tube ET where a semi-conical infusion member 218 may be used to similarly infuse (or suction out) the substances.

Figure 24A:
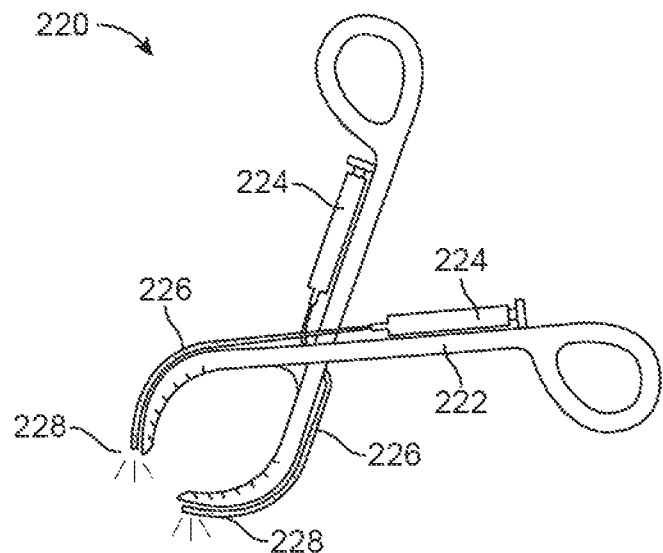
FIGS. 24A and 24B show perspective and side views of an instrument such as a hemostat which may be configured to infuse and/or evacuate a composition into proximity to an ET tube.
Figure 24B:
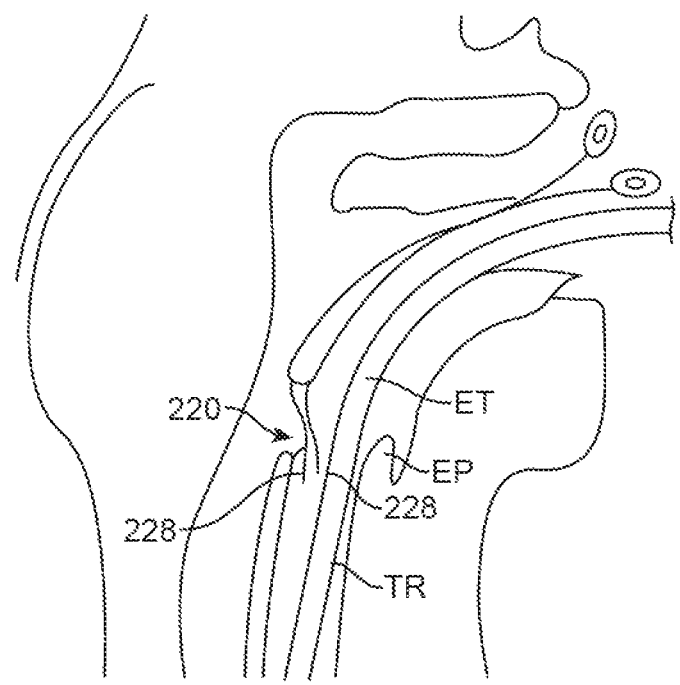

In yet another variation of an instrument which may be used to introduce or remove the substances, FIG. 24A shows a side view of an infusion instrument 220, such as a hemostat 222 having one or more reservoirs 224 with corresponding infusion lumens 226 which may extend towards the respective distal tips of the hemostat 222. The distal ends of the lumen 226 may each define respective openings 228 through which the various substances may be infused (or suctioned through). In use, the infusion instrument 220 may be inserted per-orally and can be directed to inject the composition into proximity to the epiglottis ET around the ET tube ET either with the cuff assembly 10 or separately from the assembly 10, as shown in FIG. 24B. The instrument 220 may optionally include a visualization component with a light source and a mirror to monitor the injection.

Figure 25:
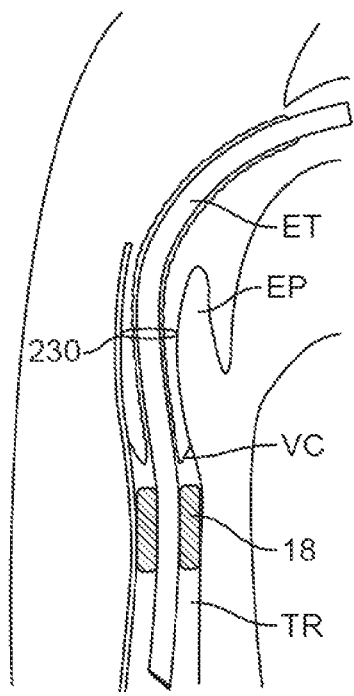
FIG. 25 shows a side view of a deployable platform which may be positioned along an ET tube to provide a platform for infusion of a composition.
Figure 26:
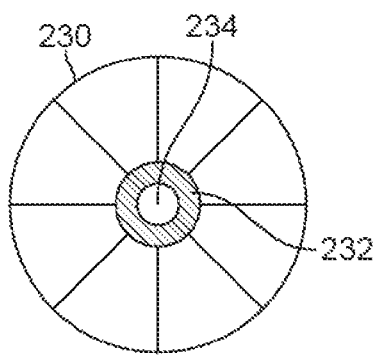
FIG. 26 shows a top view of one variation of a deployable platform.
Figure 27A:
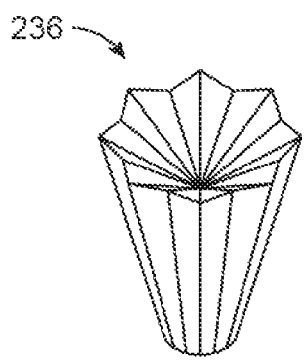
FIGS. 27A and 27B show perspective views of additional variations for deployable platforms.
Figure 27B:
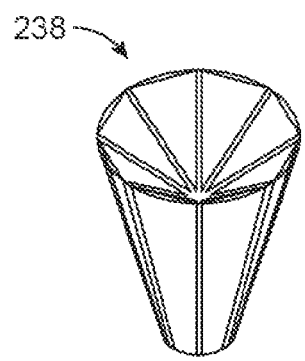
Figure 28A:
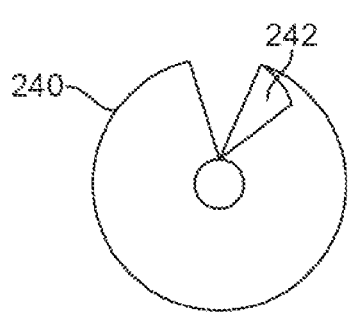
FIGS. 28A and 28B show top views of yet another variation for a deployable platform.
Figure 28B:
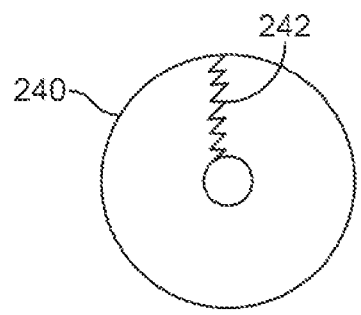

Another variation for use with the cuff assembly 10 and with the infusion of various substances is shown in the side view of FIG. 25. In this variation, a reconfigurable platform 230 may be positioned around the ET tube ET at any point between the mouth and the carina. The platform 230 may be a flexible disc 230 or cup-like structure which incorporates a seal 232 around an opening 234 for sealing against the IT tube ET and which may also conform to the trachea TR and allows for the composition to be deposited onto the platform 230, as shown in the top view of FIG. 26. The platform 230 may be slid over or upon the ET tube ET in a collapsed configuration and once suitably positioned, it may be expanded or deployed. FIG. 27A shows a foldable platform 236 and FIG. 27B shows a collapsible platform 238 either of which may be utilized. FIGS. 28A and 28B show top views of yet another platform variation 240 which defines a sealable flap 242 which may be opened and then sealed upon itself to form the platform. Once the composition is to be removed, the platform could be retrieved with the composition still upon the platform 230 with the ET tube ET remaining in place or simultaneously with ET tube ET removal.

Additionally and/or alternatively, a shield 250 having a securement member 252 may be deployed within the patient in combination with the inflatable member 14 and ET tube ET, as shown in the side view of FIG. 29. One variation of shield 250 may be seen in FIG. 30A which may comprise a biocompatible, elastic material (which may optionally have shape memory characteristics) which may be deployed to extend from the epiglottis EP and over the opening of the trachea TR to extend at least partially within the esophagus ES. The securement member 252 may comprise a simple loop for securement around the epiglottis EP or it may comprise a biocompatible adhesive for adhering the shield 250 to the mucosa and/or ET tube ET. Alternatively, the shield 250 may be secured to the ET tube ET via a sheath 258, as shown in FIG. 30B, or a wedging member 260 may be used to secure the shield 250 above or around the epiglottis EP, as shown in FIG. 30C.

In other alternatives, the shield 250 may be secured in place within the esophagus ES by incorporating magnetically attractive material within the shield. A corresponding magnetically attractive material or element 256 may be incorporated into the ET tube ET or a separate magnetically attractive member 254 may be positioned external to the patient for attracting the shield 250 and maintaining its position against the anterior wall of the esophagus ES.

In yet other alternatives, a spring-loaded membrane may be used that pushes against the esophagus ES and/or epiglottis EP. In other variations, a portion of membrane 250 may be maintained against the anterior wall of the esophagus ES by stapling, suturing, use of a weight on the distal end of the membrane 250, use of an elastic material with shape memory that bends back, adhesive, or various other mechanisms.

Methods

As mentioned above, the methods described here may comprise advancing a deployable member within or along a patient's airway to form a barrier therein. In some variations, the deployable member may comprise a cuff assembly, which may comprise an inflatable member such as those described above. For example, in some variations the inflatable member may comprise an inflation ring and a balloon. The cuff assembly may further comprise an inflation tube and an inflation port, such that the inflatable member may be inflated by introducing a gas or fluid into the inflation port (or may be deflated by withdrawing fluid therefrom).

In some variations, the deployable member may be positioned around an ET tube or laryngeal mask at a location along the patient's airway. In some instances, the deployable member may be positioned simultaneously with the ET tube or laryngeal mask. In other instances, the deployable member may be advanced along a pre-placed ET tube or laryngeal mask. The deployable member may be advanced using one or more of the delivery instruments described above. In these variations, the deployable member may be temporarily attached to the delivery instrument, and the delivery instrument may be manipulated to advance and position the inflatable member. Advancement of the deployable member may be done without direct visualization of the vocal cords, and the delivery instrument may provide tactile feedback and/or other feedback to indicate placement of the deployable member.

Figure 10A:
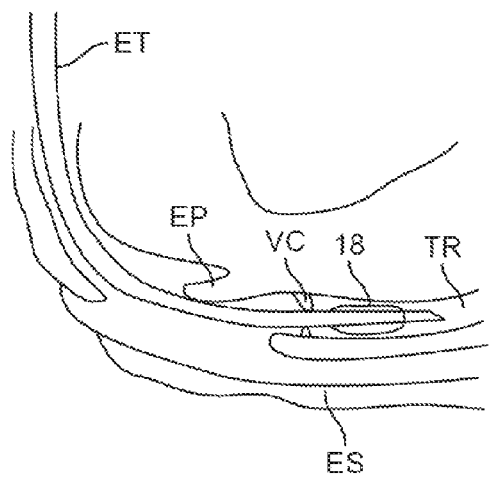
FIGS. 10A to 10C illustrate one variation for positioning a balloon via a delivery instrument along an ET tube positioned within a patient.
Figure 10B:
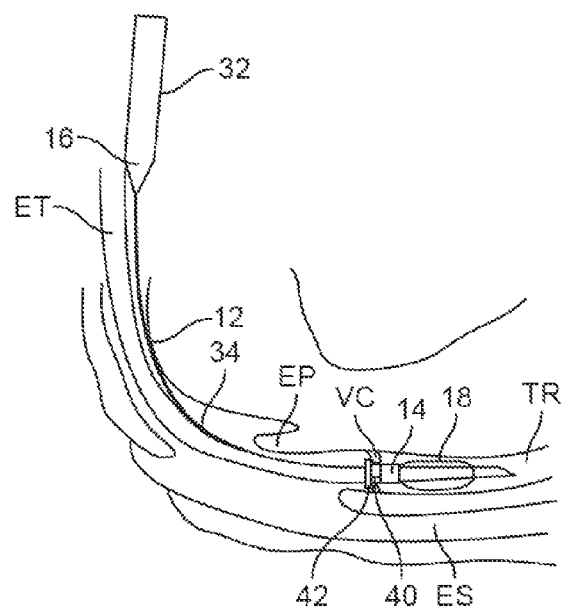
Figure 10C:
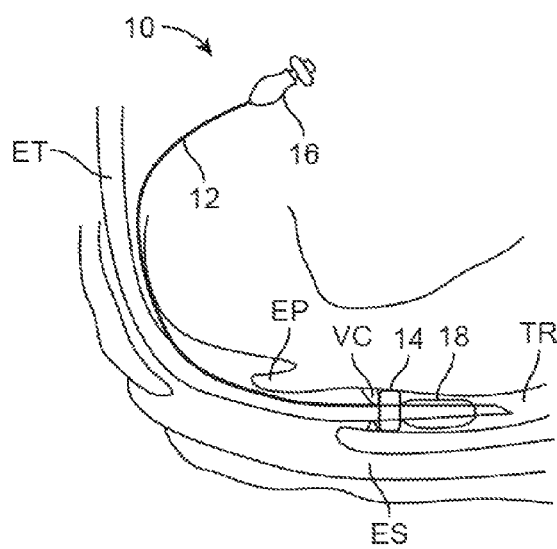

FIGS. 10A to 10C show partial cross-sectional side views illustrating one example of how the cuff assembly 10 described above may be positioned within a patient. As shown in FIG. 10A, an ET tube ET may be advanced and positioned within the trachea TR with the FT balloon 18 positioned past the patient's vocal cords VC. FIG. 10B shows how the delivery instrument 30 with the cuff assembly 10 temporarily attached thereto (such as described above) may be placed over the ET tube ET and advanced distally into and through the patient while guided by the ET tube ET. As the inflatable member 14 is guided along the ET tube ET past the vocal cords VC, the distal stop 42 may abut against the vocal cords VC to position the inflatable member 14 just past the vocal cords VC at a distance determined by the engagement member 40. The practitioner may receive the tactile feedback from the distal stop 42 positioned against the vocal cords VC as an indication that the inflatable member 14 has been appropriately positioned along the ET tube ET. While this example illustrates how the cuff assembly 10 may be advanced after intubation of the ET tube ET, the cuff assembly 10 may also be pre-positioned along the ET tube ET during intubation as well, if so desired.

Once the inflatable member 14 has been suitably positioned, the inflatable member 14 may be inflated and secured against the tissue walls of the trachea TR and ET tube ET and the inflation port 16 and lumen 12 may be released from delivery instrument 30 which may then be removed from the patient, as shown in FIG. 10C. Alternatively, delivery instrument 30 may be removed prior to inflation of the inflatable member 14 or during inflation of the inflatable member 14 as well. With the cuff assembly 10 in place, a suitable barrier may be provided to prevent or inhibit aspiration into the trachea TR.

Once the patient is to be extubated, the inflatable member 14 may be deflated and the cuff assembly 10 may be simply removed from ET tube ET by applying tension to inflation tube 12 to pull inflatable member 14 proximally along ET tube ET for removal or replacement. Alternatively, both the inflatable member 14 and ET balloon 18 may be deflated and both the cuff assembly 10 and ET tube ET may be removed simultaneously from the patient's airway.

The applications of the devices and methods discussed above are not limited to VAP but may include any number of further treatment applications. For example, the devices and methods described above may be used to place a barrier member along a nasogastric or orogastric tubes to create a seal in the oropharyngeal space, esophagus, or stomach. Moreover, such devices and methods may be applied to other treatment sites within the body, e.g., esophagus, urinary tract, etc. Modification of the above-described assemblies and methods for carrying out the invention, combinations between different variations as practicable, and variations of aspects of the invention that are obvious to those of skill in the art are intended to be within the scope of the claims.

What is claimed is:

1. A positioning handle assembly, comprising:
   an elongate shaft which presents a profile for per-oral insertion into a trachea of a subject;
   a distal stop attached to a distal end of the shaft, where the distal stop extends at least partially from a surface of the shaft and presents a stopping surface which is sized to prevent passage of the distal stop through vocal cords or laryngeal inlet of the subject; and,
   a cuff engagement member which extends distally from the distal stop at a distance and forms an edge for engagement with a cuff assembly, where the distal stop is partially circumferential extending from the surface of the shaft and wherein the cuff engagement member forms a partial tubular member such that the distal stop and cuff engagement member define an opening sized to receive an endotracheal tube therealong such that disengagement of the distal stop from the endotracheal tube allows for disengagement of the elongate shaft from the endotracheal tube via the opening, and
   where the distance is sized such that the cuff engagement member extends past the vocal cords when the distal stop contacts the vocal cords or laryngeal inlet.

2. The positioning handle assembly of claim 1 wherein the elongate shaft comprises an arcuate shaft which defines a preformed curvature which presents an atraumatic profile.

3. The positioning handle assembly of claim 1 wherein the shaft has a preformed radius of curvature ranging from 12 in. to 300 in.

4. The positioning handle assembly of claim 1 wherein the shaft has a length ranging from 5 in. to 20 in.

5. The positioning handle assembly of claim 1 wherein the distal stop has a width of about 20 mm in a transverse direction relative to a length of the shaft.

6. The positioning handle assembly of claim 1 wherein the distal stop is configured to have a shape approximating a laryngeal inlet.

7. The positioning handle assembly of claim 1 wherein the stopping surface is transversely oriented relative to the shaft.

8. The positioning handle assembly of claim 1 wherein the cuff engagement member has a length of about 2 mm to 1 cm.

9. The positioning handle assembly of claim 1 further comprising the cuff assembly, wherein the cuff assembly comprises an inflation ring having an inflatable member disposed along an exterior surface of the inflation ring.

10. The positioning handle assembly of claim 9 further comprising an inflation tube fluidly coupled to the inflation ring and extending along a channel defined along the shaft.

11. The positioning handle assembly of claim 9 wherein the cuff assembly further comprises a sealing sleeve attached to the inflation ring.

12. The positioning handle assembly of claim 9 wherein the cuff assembly defines a narrowed distal end and a tapered proximal end.

13. The positioning handle assembly of claim 9 wherein the cuff assembly defines a narrowed distal end and a narrowed proximal end.

14. The positioning handle assembly of claim 1 wherein the cuff assembly is impregnated or coated with an agent.

15. The positioning handle assembly of claim 1 further comprising a sealing sleeve attached to the cuff assembly for sealing about the endotracheal tube.

16. The positioning handle assembly of claim 1 further comprising a handle coupled to a proximal end of the shaft, the handle defining a channel for receiving an inflation port.

17. The positioning handle assembly of claim 16 wherein the handle is further configured to receive a fluid reservoir.

18. The positioning handle assembly of claim 1 further comprising an endotracheal tube upon which the cuff engagement member is slidable therealong.

19. A positioning handle assembly, comprising:
an elongate arcuate shaft which defines a preformed curvature which presents an atraumatic profile for per-oral insertion into a trachea of a subject;
a distal stop attached to a distal end of the shaft, where the distal stop extends circumferentially and presents a stopping surface which is transversely oriented relative to the shaft and where the distal stop is sized to prevent passage of the distal stop through vocal cords of the subject; and,
a cuff engagement member which extends distally from the distal stop at a distance and forms an edge for engagement with a cuff assembly, where the distal stop is partially circumferential extending from a surface of the shaft and wherein the cuff engagement member forms a partial tubular member such that the distal stop and cuff engagement member define an opening sized to receive an endotracheal tube therealong such that disengagement of the distal stop from the endotracheal tube allows for disengagement of the elongate shaft from the endotracheal tube, and where the distance is sized such that the cuff engagement member extends past the vocal cords when the distal stop contacts the vocal cords.

20. The positioning handle assembly of claim 19 wherein the shaft has a preformed radius of curvature ranging from 12 in. to 300 in.

21. The positioning handle assembly of claim 19 wherein the shaft has a length ranging from 5 in. to 20 in.

22. The positioning handle assembly of claim 19 wherein the distal stop has a width of about 20 mm in a transverse direction relative to a length of the shaft.

23. The positioning handle assembly of claim 19 wherein the distal stop is configured to have a shape approximating a laryngeal inlet.

24. The positioning handle assembly of claim 19 wherein the cuff engagement member has a length of about 2 mm to 1 cm.

25. The positioning handle assembly of claim 19 further comprising the cuff assembly, wherein the cuff assembly comprises an inflation ring having an inflatable member disposed along an exterior surface of the inflation ring.

26. The positioning handle assembly of claim 25 wherein the cuff assembly further comprises a sealing sleeve attached to the inflation ring.

27. The positioning handle assembly of claim 25 further comprising an inflation tube fluidly coupled to the inflation ring and extending along a channel defined along the shaft.

28. The positioning handle assembly of claim 19 further comprising the cuff assembly, wherein the cuff assembly defines a narrowed distal end and a tapered proximal end.

29. The positioning handle assembly of claim 19 further comprising the cuff assembly, wherein the cuff assembly defines a narrowed distal end and a narrowed proximal end.

30. The positioning handle assembly of claim 19 further comprising the cuff assembly, wherein the cuff assembly is impregnated or coated with an agent.

31. The positioning handle assembly of claim 19 further comprising a handle coupled to a proximal end of the shaft, the handle defining a channel for receiving an inflation port.

32. The positioning handle assembly of claim 31 wherein the handle is further configured to receive a fluid reservoir.

33. The positioning handle assembly of claim 19 further comprising an endotracheal tube upon which the cuff engagement member is slidable therealong.

34. A positioning handle assembly, comprising:
an elongate shaft which presents a profile for per-oral insertion into a trachea of a subject;
a distal stop attached to a distal end of the shaft, where the distal stop extends at least partially from a surface of the shaft and presents a stopping surface which is shaped for placement against a laryngeal inlet of the subject to prevent passage of the distal stop therethrough; and,
a cull engagement member which extends distally from the distal stop at a distance and forms an edge for engagement with a cuff assembly, where the distal stop is partially circumferential extending from the surface of the shaft and wherein the cuff engagement member forms a partial tubular member such that the distal stop and cuff engagement member define an opening sized to receive an endotracheal tube therealong such that disengagement of the distal stop from the endotracheal tube allows for disengagement of the elongate shaft from the endotracheal tube, and where the distance is sized such that the cuff engagement member extends past the vocal cords when the distal stop contacts the laryngeal inlet.

35. The positioning handle assembly of claim 34 wherein the distal stop further defines an upper surface apposed to the stopping surface, where the stopping surface and upper surface are radially extending from the surface of the shaft.

36. The positioning handle assembly of claim 34 wherein the stopping surface of the distal stop presents a curved surface.

37. The positioning handle assembly of claim 34 wherein the stopping surface is transversely oriented relative to the shaft.

38. The positioning handle assembly of claim 34 wherein the cuff engagement member has a length of about 2 mm to 1 cm.

* * * * *